United States Patent
Bayley et al.

(10) Patent No.: US 11,549,097 B2
(45) Date of Patent: Jan. 10, 2023

(54) PHASE TRANSFER OF A CARGO LADEN SCAFFOLD

(71) Applicant: Oxford University Innovation Limited, Oxford (GB)

(72) Inventors: Hagan Bayley, Oxford (GB); Sam Olof, Oxford (GB); Alexander D. Graham, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 523 days.

(21) Appl. No.: 16/081,305

(22) PCT Filed: Feb. 28, 2017

(86) PCT No.: PCT/GB2017/050542
§ 371 (c)(1),
(2) Date: Aug. 30, 2018

(87) PCT Pub. No.: WO2017/149297
PCT Pub. Date: Sep. 8, 2017

(65) Prior Publication Data
US 2019/0024034 A1    Jan. 24, 2019

(30) Foreign Application Priority Data

Mar. 1, 2016 (GB) ........................ 1603560
Mar. 1, 2016 (GB) ........................ 1603564

(51) Int. Cl.
| | | |
|---|---|---|
| C12N 5/00 | (2006.01) | |
| C12M 1/26 | (2006.01) | |
| C12M 1/12 | (2006.01) | |
| C12M 3/02 | (2006.01) | |
| C12N 5/16 | (2006.01) | |
| B33Y 30/00 | (2015.01) | |
| A61L 27/38 | (2006.01) | |
| A61L 27/52 | (2006.01) | |

(52) U.S. Cl.
CPC ............ *C12N 5/0062* (2013.01); *A61L 27/38* (2013.01); *A61L 27/52* (2013.01); *B33Y 30/00* (2014.12); *C12M 3/02* (2013.01); *C12M 25/14* (2013.01); *C12M 33/00* (2013.01); *C12N 5/16* (2013.01); *C12N 2531/00* (2013.01); *C12N 2533/52* (2013.01); *C12N 2533/54* (2013.01); *C12N 2533/76* (2013.01); *C12N 2535/10* (2013.01)

(58) Field of Classification Search
CPC .................................................. C12N 5/0062
See application file for complete search history.

(56) References Cited

U.S. PATENT DOCUMENTS

| | | |
|---|---|---|
| 6,017,758 A | 1/2000 | Hasel, III et al. |
| 6,114,153 A | 9/2000 | Shukla et al. |
| 2002/0155606 A1 | 10/2002 | Okamoto et al. |
| 2005/0032118 A1 | 2/2005 | Self et al. |
| 2007/0069408 A1 | 3/2007 | Cheng et al. |
| 2007/0099840 A1 | 5/2007 | Ulijn et al. |
| 2007/0178448 A1 | 8/2007 | Tsao et al. |
| 2007/0224273 A1 | 9/2007 | Xu et al. |
| 2011/0306110 A1 | 12/2011 | Takeuchi et al. |
| 2013/0202802 A1 | 8/2013 | Gazda et al. |
| 2014/0271843 A1* | 9/2014 | Ma ........................... A61P 9/00 424/463 |

(Continued)

FOREIGN PATENT DOCUMENTS

| | | |
|---|---|---|
| CN | 1520306 | 8/2004 |
| CN | 1994478 | 7/2011 |

(Continued)

OTHER PUBLICATIONS

Merriam-Webster definition: dispose; retrieved from the internet Apr. 3, 2021: https://www.merriam-webster.com/dictionary/dispose (Year: 2021).*
T&T Scientific, Product Information for DPhPC, retrieved from the internet Apr. 6, 2021: https://ttscientific.com/products/dphpc-4me-16-0-pc-1-2-diphytanoyl-sn-glycero-3-phosphatidylcholine (Year: 2021).*
Varghese et al., The Journal of Thoracic and Cardiovascular Surgery, Feb. 2015, pp. 470-472 (Year: 2015).*
English Translation of WO 2013/113883, 5 pages (Year: 2013).*
Gazda et al., Cell Transplantation, vol. 16, pp. 609-620, 2007 (Year: 2007).*
Abkarian et al., "Continuous droplet interface crossing encapsulation (cDICE) for high throughput monodisperse vesicle design" *Soft Matter* 7, 4610 (2011).

(Continued)

*Primary Examiner* — Evelyn Y Pyla
(74) *Attorney, Agent, or Firm* — Hamilton, Brook, Smith & Reynolds, P.C.

(57) ABSTRACT

The present invention relates to a process for producing a composition comprising an aqueous medium and, disposed in the aqueous medium, a first volume of a first hydrogel, which process comprises: (i) providing a composition comprising a first hydrophobic medium and, disposed in the first hydrophobic medium, a first volume of a first hydrogel; (ii) disposing a volume of an aqueous composition comprising a hydrogel compound around the first volume of the first hydrogel; (iii) allowing the aqueous composition comprising the hydrogel compound to form a gel and thereby forming a hydrogel object, which hydrogel object comprises the first volume of the first hydrogel and a second volume of a second hydrogel, which second volume of the second hydrogel is disposed around the first volume of the first hydrogel; and (iv) transferring the hydrogel object from the first hydrophobic medium to an aqueous medium and thereby producing the composition comprising the aqueous medium and, disposed in the aqueous medium, the first volume of the first hydrogel. The invention further provides a hydrogel object, which hydrogel object comprises a first volume of a first hydrogel and a second volume of a second hydrogel, which second volume of the second hydrogel is disposed around the first volume of the first hydrogel.

25 Claims, 5 Drawing Sheets

(56) References Cited

U.S. PATENT DOCUMENTS

| | | |
|---|---|---|
| 2014/0356289 A1 | 12/2014 | Baylet et al. |
| 2015/0217024 A1 | 8/2015 | Wang et al. |
| 2015/0248949 A1 | 9/2015 | Bayley et al. |
| 2019/0062729 A1 | 2/2019 | Bayley et al. |
| 2019/0093071 A1 | 3/2019 | Bayley et al. |

FOREIGN PATENT DOCUMENTS

| | | | |
|---|---|---|---|
| CN | 104353123 | 2/2015 | |
| CN | 104936682 | 9/2015 | |
| WO | 02062357 | 8/2002 | |
| WO | WO 2007/043048 | 4/2007 | |
| WO | 2011151832 A1 | 12/2011 | |
| WO | WO 2013/064837 A1 | 5/2013 | |
| WO | WO 2013/113883 * | 8/2013 | ............... C12N 5/00 |
| WO | 2014064444 | 5/2014 | |
| WO | WO 2014/064459 | 5/2014 | |
| WO | WO 2014/064461 | 5/2014 | |
| WO | WO 2014/087175 | 6/2014 | |
| WO | WO 2014/132262 | 9/2014 | |
| WO | WO 2014/200997 | 12/2014 | |
| WO | WO 2016/142637 | 9/2016 | |

OTHER PUBLICATIONS

Atala et al. "3D bioprinting of tissues and organs", Nat Biotechnol, 32(8): 773-785 (2014).
Bayley et al. "Droplet interface bilayers", Mol. Biosyst. 4, 1191-1208 (2008).
Calvert, P., "Printing Cells", Science, 318, 208-209 (2007).
Derby, B., "Printing and Prototyping of Tissues and Scaffolds", Science 338, 921-926 (2012).
Duarte Campos et al. "Three-dimensional printing of stem cell-laden hydrogels submerged in a hydrophobic high-density fluid", Biofabrication 5, 015003, 11 pages (2013).
Duarte Campos et al. "The Stiffness and Structure of Three-Dimensional Printed Hydrogels Direct the Differentiation of Mesenchymal Stromal Cells Toward Adipogenic and Osteogenic Lineages", Tissue Engineering Part A 21(3 and 4): 740-756 (2015).
Elani et al. "Vesicle-based artificial cells as chemical microreactors with spatially segregated reaction pathways", Nat. Commun. 5, 1-5 (2014).
Elani et al., "Engineering multi-compartment vesicle networks", Chem. Sci. 4, 3332-3338 (2013).
Elani et al., "Novel technologies for the formation of 2-D and 3-D droplet interface bilayer networks", Lab Chip 12, 3514-20 (2012).
Foty, R, J. "A simple hanging drop cell culture protocol for generation of 3d spheroids", Vis. Exp. 20, 4-7, 2011.
Gurkan et al. "Engineering Anisotropic Biomimetic Fibrocartilage Microenvironment by Bioprinting Mesenchymal Stem Cells in Nanoliter Gel Droplets", Mol. Pharm. 11, 2151-9 (2014).
Haraguchi, Y, "Scaffold-free tissue engineering using cell sheet technology", RSC Adv. 2, 2184, (2012).
Gudapate, H et al. "A comprehensive review on droplet-based bioprinting: Past, present and future", Biomaterials 102, 20-42 (2016).
Hwang et al. "Asymmetric Droplet Interface Bilayers", J. Am. Chem. Soc. 130, 15854-64 (2008).
Ito et al., "Dynamical formation of lipid bilayer vesicles from lipid-coated droplets across a planar monolayer at an oil/water interface", Soft Matter 9, 9539 (2013).
Kolesky et al., "3D Bioprinting of Vascularized, HeterogeneousCell-Laden Tissue Constructs", Adv. Mater. 26, 3124-30 (2014).
Lancaster et al., "Organogenesis in a dish: Modeling development and disease using organoid technologies", Science (80), 345(6194): 1247125 11 pages (2014).
Li et al. "Rapid formation of a supramolecular polypeptide-DNA hydrogel for in situ three-dimensional multilayer bioprinting", Angew. Chemie Int. Ed. 54, 1-6a (2015).

Maglia et al., "Droplet networks with incorporated protein diodes show collective properties", Nat. Nanotechnol. 4, 437-440 (2009).
Mannoor et al. "3D Printed Bionic Ears" Nano Lett. 13, 2634-2639 (2013).
Norotte et al. "Scaffold-free vascular tissue engineering using bioprinting", Biomaterials 30(2009) 5910-5917.
Onoe et al, "Cell-laden microfibers for bottom-up tissue engineering", Drug Discov. Today 20, 236-246 (2015).
Onoe, H, "Metre-long cell-laden microfibres exhibit tissue morphologies and functions", Nat. Mater. 12, 584-590, (2013).
Ozbolat et al. "Bioprinting toward organ fabrication: Challenges and Future Trends", IEEE Trans. Biomed. Eng. 60(3): 691-699, 79109 (2013).
Pati et al., "Printing three-dimensional tissue analogues with decellularized extracellular matrix bioink", Nat. Commun. 5:3935, 11 pages (2014).
Pautot et al., "Engineering asymmetric vesicles", Proc. Natl. Acad. Sci. U.S.A. 100, 10718-10721, 100(19) (2003).
Syeda et al., "Screening blockers against a potassium channel with a droplet interface bilayer array", J. Am. Chem. Soc. 130, 15543-15548 (2008).
Villar et al., "Formation of droplet networks that function in aqueous environments", Nat. Nanotechnol. 6, 803-808 (2011).
Villar et al., "A tissue-like printed materials", Science 340, 48-52 (2013).
Walde et al., "Giant Vesicles: Preparations and Applications", Chembiochem 11, 848-65 (2010).
Yamada et al., "Spontaneous Transfer of Phospholipid-Coated Oil-in-Oil and Water-in-Oil Micro-Droplets through an Oil/Water Interface", Langmuir 22, 9824-9828 (2006).
Yanagisawa et al., "Oriented Reconstitution of a Membrane Protein in a Giant unilamellar vesicle: experimental verification with the potassium channel KcsA", J. Am. Chem. Soc. 133, 11774-11779(2011).
Arkin, "Synthetic cell biology", Curr Opin Biotechnol. 12(6)638-44 (2001).
Bai et al., "Photocleavage of a 2-nitrobenzyl linker bridging a fluorophore to the 5' end of DNA", PNAS, vol. 100, No. 2, 409-413 (2003).
Beckert, B., et al., "Synthesis of RNA by in vitro transcription", Methods Mol. Biol. 703: pp. 29-41 (2011), [doi: 10.1007/978-1-59745-248-9_3].
Booth, M.J., "Light-activated communication in synthetic tissues", Sci. Adv. 2, 4 (2016).
Boshart et al., "A very strong enhancer is located upstream of an immediate early gene of human cytomegalovirus", Cell, 41:521-530 (1985).
Bubeck, P., et al., "Rapid cloning by homologous recombination in vivo", Nucleic Acids Res. 21, 3601 (1993).
Dahl et al., "Microfluidic Strategies for Understanding the Mechanics of Cells and Cell-Mimetic Systems" Annu Rev Chem Biomol Eng. 6:293-317 (2015).
Diguet, A., et al., "UV-induced bursting of cell-sized multicomponent lipid vesicles in a photosensitive surfactant solution", J. Am. Chem. Soc. 134, 4898 (2012).
Estevez-Torres, A., et al., "Sequence-independent and reversible photocontrol of transcription/expression systems using a photosensitive nucleic acid binder", Proc.Natl. Acad. Sci. U. S. A. 106, 12219 (2009).
Fedoryshin et al., "Near-Infrared-Triggered Anti cancer Drug Release from Upconverting Nanoparticles", ACS Applied Materials & Interfaces, 6, 13600-13606 (2014).
Fujii, S., et al., "In vitro evolution of alpha-hemolysin using a liposome display", Proc. Natl. Acad. Sci. U. S. A. 110, 16796 (2013).
Gorka et al., "A Near-IR Uncaging Strategy Based on Cyanine Photochemistry" J. Am. Chem. Soc, 136, 14153-14159 (2014).
Hemphill, J., et al., "Site-Specific Promoter Caging Enables Optochemical Gene Activation in Cells and Animals", J. Am. Chem. Soc. 136 (2014).
Holden, M.A., et al., Functional bionetworks from nanoliter water droplets, J. Am. Chem. Soc. 129, 8650 (2007).

(56) References Cited

OTHER PUBLICATIONS

Howarth, M., et al., "A monovalent streptavidin with a single femtomolar biotin binding site", Nat. Methods 3, 267 (2006).
Hwang, W.L., et al., "Electrical behavior of droplet interface bilayer networks: experimental analysis and modeling", J. Am. Chem. Soc. 129, 11854-11864 (2007).
Ichihashi, N., "Darwinian evolution in a translation-coupled RNA replication system within a cell-like compailment", Nat. Commun, 4, 2494 (2013).
International Search Report for International Application No. A114, "Printing of a Cellularised Scaffold": dated May 23, 2017.
International Search Report for International Application No. PCT/GB2017/050542, "Phase Transfer of a Cargo Laden Scaffold": dated May 15, 2017.
International Search Report for International Application No. PCT/GB2017/050538, "Improved Promoters and Compositions": dated Jun. 30, 2017.
Kaneda, M., et al., "Direct formation of proteo-liposomes by in vitro synthesis and cellular cytosolic delivery with connexin-expressing liposomes", Biomaterials 30, 3971 (2009).
Karzbrun, E., et al., "Programmable on-chip DNA compartments as artificial cells", Science 345, 829 (2014).
Konermann et al., "Optical control of mammalian endogenous transcription and epigenetics states", Nature, 500(7463), 472-476 (2013).
Kröck, L., et al., "Photoinduced Transcription by Using Temporarily Mismatched Caged Oligonucleotides", Angew Chem Int Ed Engl. 471-473, 44 (2005).
Lentini, R., et al., "Integrating artificial with natural cells to translate chemical messages that direct *E. coli* behaviour", Nat. Commun. 5, 4012 (2014).
Liu, M., "Azobenzene-tethered T7 promoter for efficient photoregulation of transcription", J. Am. Chem. Soc. 128, 1009 (2006).
Lu, W. C., "In vitro selection of proteins via emulsion compai Iments. Methods", 60, 75 (2013).
Maglia, G et al., "Analysis of single nucleic acid molecules with protein nanopores", Method. Enzymol. 475, 591-623 (2010).
Monroe, W. T., et al., "Targeting expression with light using caged DNA", J. Biol. Chem. 274, 30 (1999).
Murtas, "Artificial assembly of a minimal cell", Mol Biosyst. 5(11): 1292-7 (2009).
Murtas, G., et al., "Protein synthesis in liposomes with a minimal set of enzymes", Biochem. Biophys. Res. Commun. 363, 12 (2007).
Nishikawa, T., et al., "Construction of a gene screening system using giant unilamellar liposomes and a fluorescence-activated cell sorter", Anal. Chem. 84, 5017 (2012).
Noireaux, V., et al., "A vesicle bioreactor as a step toward an artificial cell assembly", Proc. Natl. Acad. Sci. U. S. A. 101, 17669 (2004).
Notification Concerning Transmittal of Copy of International Preliminary Report on Patentability for International Application No. PCT/GB2017/050542, "Phase Transfer of a Cargo Laden Scaffold": dated Sep. 13, 2018.
Notification Concerning Transmittal of International Preliminary Report on Patentability for International Application No. PCT/GB2017/050538, "Improved Promoters and Compositions": dated Sep. 13, 2018.
Notification Concerning Transmittal of Copy of International Preliminary Report on Patentability for International Application No. PCT/GB2017/050541, "Printing of a Cellularised Scaffold": dated Sep. 13, 2018.
O'Hare et al., "Transformation of mouse fibroblasts to methotrexate resistance by a recombinant plasmid expressing a prokaryotic dihydrofolate reductase", Proc. Natl. Acad. Sci., vol. 78(3), p. 1527-31 (1981).
Olejnik, J., et al., "Photocleavable biotin derivatives: a versatile approach for the isolation of biomolecules", Proc. Natl. Acad. Sci. U. S. A. 92, 7590 (1995).
Panyam et al., "Biodegradable nanoparticles for drug and gene delivery to cells and tissue", Adv Drug Deliv Rev, Sep. 13, 2012.

Presentation by M. Booth at the 'Compartmentalisation & Confinement in Biological Systems' workshop, run by the EPSRC Physics of Life network, from the 21st/22nd Sep. 2015 at Cripps Court, Magdalene College, Cambridge University.
Reimao-Pinto, M.M., et al., "Dual-color control of nucleotide polymerization sensed by a fluorescence actuator", Photochem. Photobiol. Sci. 13, 751-756 (2014).
Sanzone, A. P., t al., "Assessing the biocompatibility of click-linked DNA in *Escherichia coli*", Nucleic Acids Res. 40, 10567 (2012).
Schindler et al., "Photo-activatable Cre recombinase regulates gene expression in vivo", Nature Scientific Reports, 5:13627 (2015).
Seemann, R., et al., "Droplet based microfluidics", Reports on Progress in Physics 75 (2012).
Shimizu, Y., et al., "Cell-free translation reconstituted with purified components", Nat. Biotechnol. 19, 751-755 (2001).
Shimizu, Y., et al., "Protein synthesis by pure translation systems", Methods 36, 299 (2005).
Squires T. M., et al., "Microfluidics: Fluid physics at the nanoliter scale", Rev. Mod. Phys. 77, 977-1026 (2005).
Stano, "Minimal cells: relevance and interplay of physical and biochemical factors", Biotechnol J. 6(7):850-9 (2011).
Stanton-Humphreys et al., "Wavelength-orthogonal photolysis of neurotransmitters in vitro", Chem. Commun. 48, 657-659 (2012).
Takebe et al., "SRa Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Mol. Cell. Biol, vol. 8(1), p. 466-472 (1988).
Tawfik, D.S., et al., "Man-made cell-like compartments for molecular evolution", Nat. Biotechnol. 16, 652 (1998).
Wang et al., "Spatiotemporal control of gene expression by a light-switchable transgene system", Nature Methods, vol. 9, No. 3 (2012).
Whitesides, G.M., "The origins and the future of microfluidics", Nature 442, 7101:368-373 (2006).
Written Opinion for International Application No. PCT/GB2017/050542, "Phase Transfer of a Cargo Laden Scaffold": dated May 15, 2017.
Written Opinion for International Application No. PCT/GB2017/050538, "Improved Promoters and Compositions", dated Sep. 8, 2018.
Written Opinion for International Application No. PCT/GB2017/050541, "3D Printing of a Cellularised Scaffold", dated Sep. 8, 2018.
Yamaguchi, S., et al., "Control of gene expression using caged plasmids with functionalized photo-cleavable linkers", J. Biosci. Bioengineer. 108 (2009).
Zhang, Y., et al., "DNA cloning by homologous recombination in *Escherichia coli*", Nat. Biotechnol. 18, 1314 (2000).
Sotiropoulou, P.A., et at., "Characterization of the Optimal Culture Conditions for Clinical Scale Production of Human Mesenchymal Stem Cells", Stem Cells 2006: 24:462-471.
Office Action for U.S. Appl. No. 16/081,301 "3D Printing of a Cellularised Scaffold" dated Jul. 6, 2021.
Kamiya, et al., "Synthetic Gene Involving Azobenzene-Tethered T7 Promoter for the Photocontrol of Gene Expression by Visible Light," ACS Synth. Biol., 4:365-370 (2015).
Drepper, Thomas, et al., "Lights on and action! Controlling microbial gene expression by light", App. Microbiol. Biotechnol (2011) 90: 23-40.
Hobartner, C., et al., "Modulation of RNA Tertiary Folding by Incorporation of Caged Nucleotides", Angew. Chern, 2005, 117, 7471-7475.
Liang, et al., "Effective photoregulation of gene expression by photoresponsive T7 promoter", Nucleic Acids Symposium, Series No. 51, 349-350 (2007).
Timko, et al. "Light regulation of plant gene expression by an upstream enhancer-like element", 1985, vol. 318, p. 579-582.
Yamaguchi, S., et al., "Light-activated gene expression from site-specific caged DNA with a biotinylated photolabile protection group", Chem. Commun., 2010, 46, 2244-2246.
Office Action for U.S. Appl. No. 16/081,292 "Improved Promoters and Compositions" dated Nov. 10, 2021.

(56) References Cited

OTHER PUBLICATIONS

Final Office Action for U.S. Appl. No. 16/081,301 "3D Printing of a Cellularised Scaffold" dated Jan. 25, 2022.

\* cited by examiner

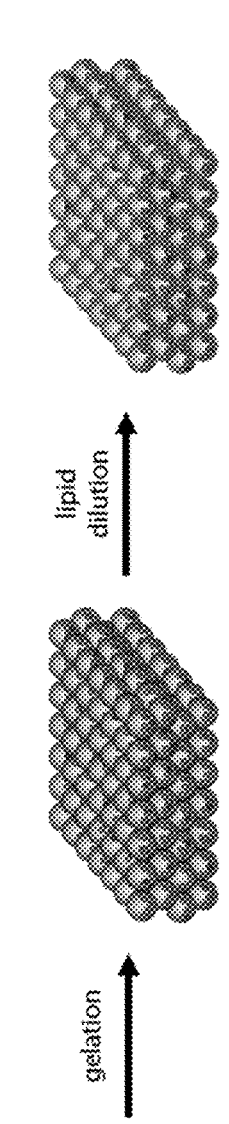
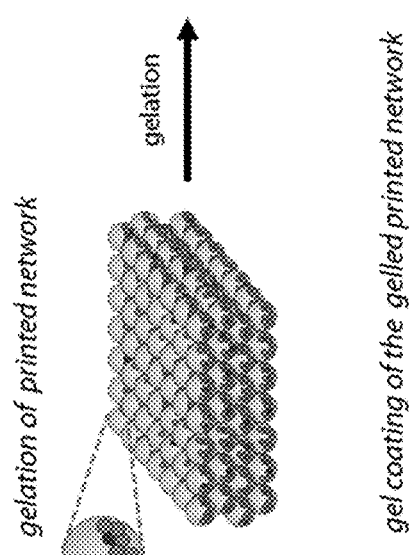
FIG. 1A
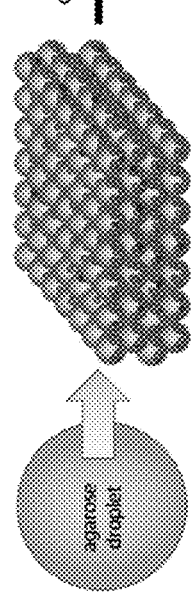
FIG. 1B
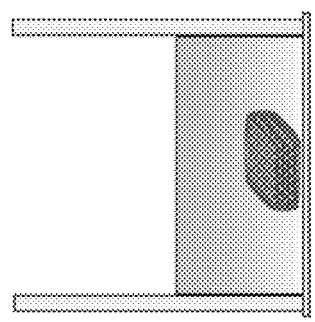
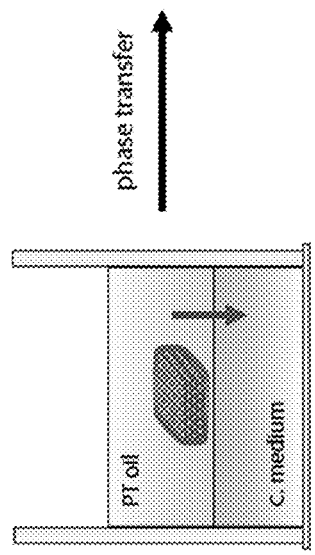
FIG. 1C

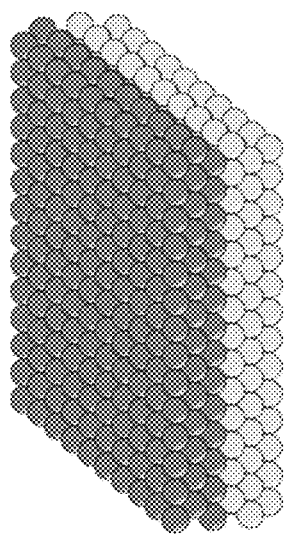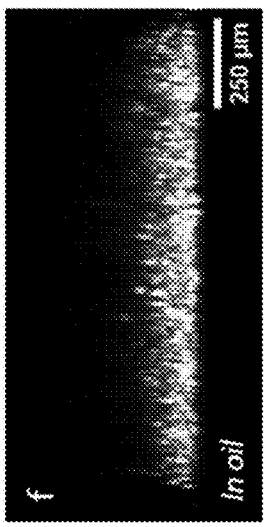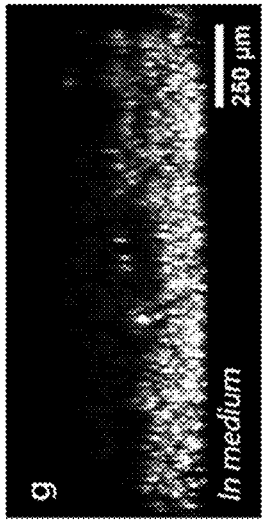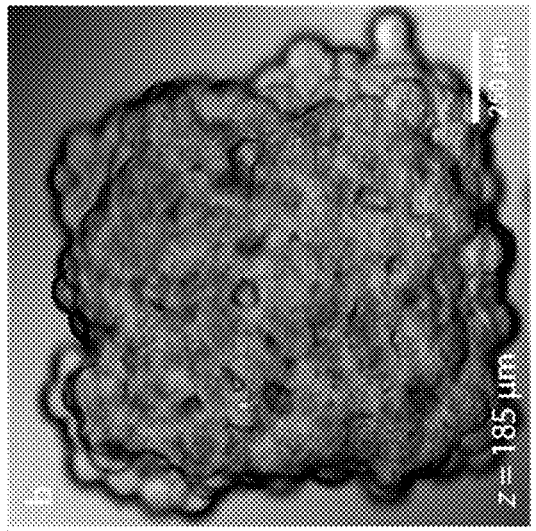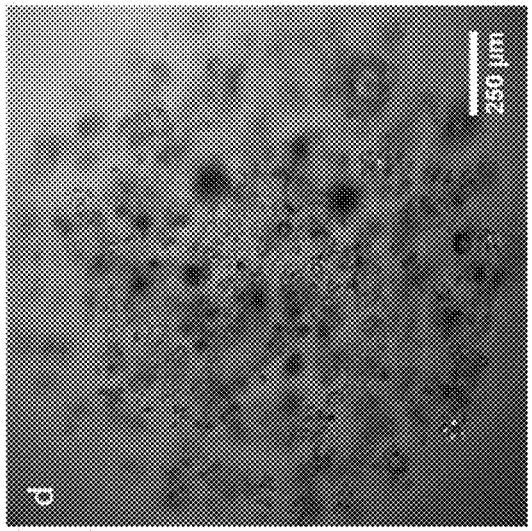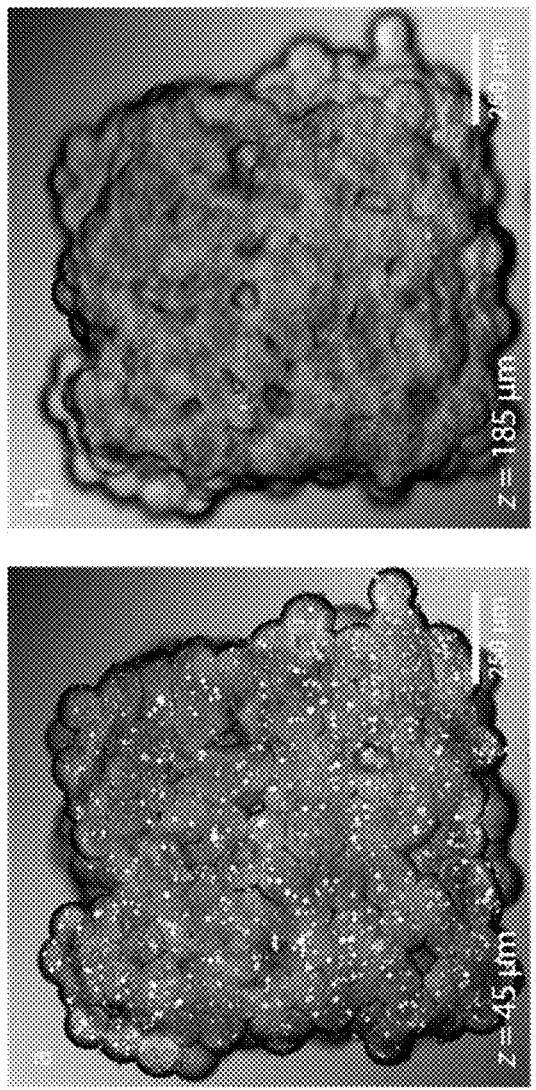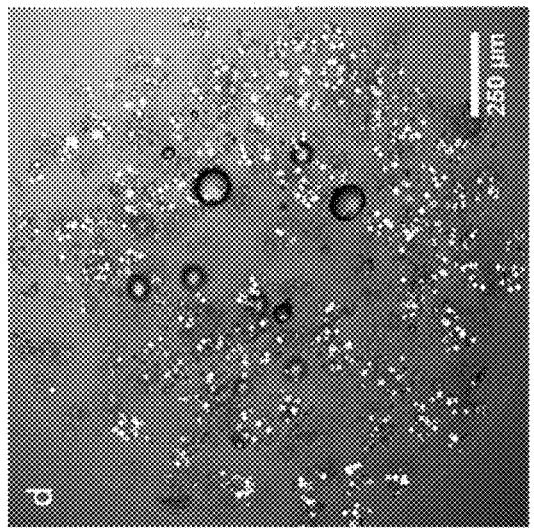

PHASE TRANSFER OF A CARGO LADEN SCAFFOLD

RELATED APPLICATIONS

This application is the U.S. National Stage of International Application No. PCT/GB2017/050542, filed Feb. 28, 2017, which designates the U.S., published in English, and claims priority under 35 U.S.C. § 119 or 365(c) to GB Application No. 1603564.4, filed Mar. 1, 2016 and GB Application No. 1603560.2, filed Mar. 1, 2016. The entire teachings of the above applications are incorporated herein by reference.

FIELD OF THE INVENTION

The present invention relates to a process for producing a composition comprising an aqueous medium and, disposed in the aqueous medium, a first volume of a first hydrogel. The invention also relates to a hydrogel object, which hydrogel object comprises a first volume of a first hydrogel and a second volume of a second hydrogel, which second volume of the second hydrogel is disposed around the first volume of the first hydrogel.

BACKGROUND OF THE INVENTION

It has been demonstrated previously that patterned droplet networks containing thousands of pico-litre (pL) volume droplets can be formed in lipid-in-oil solution using a lab-made 3D droplet printer (Villar, G., Graham, A. D. & Bayley, H. A tissue-like printed material. *Science* 340, 48-52 (2013) and WO 2014/087175). As previous droplet structures were primarily fabricated within a bulk oil solution, they were susceptible to dehydration which can cause coalescence and loss of the original pattern. Use of hydration chambers can reduce such problems, as can keeping the structure at the dew point, but these methods are ultimately restrictive to experimentation and may limit application. Additionally, structures confined to bulk oil also have limited communication with the bulk phase. This has been partly circumvented through fabrication of structures such as multisomes (Villar, G., Heron, A. J. & Bayley, H. Formation of droplet networks that function in aqueous environments. *Nat. Nanotechnol.* 6, 803-8 (2011)), i.e. droplet networks made in a oil drop suspended in a bulk aqueous phase, which were shown to be responsive to changes in pH and could exchange molecules with the bulk phase. However, due to the production method, multisomes have restricted geometries which are currently limited to nested spheroids. Hence, there is a necessity to phase transfer hydrogel droplet networks to retain a complex architecture over time and for the exchange of molecules into the structure.

The inventors have specifically aimed to phase transfer volumes of hydrogels such as 3D patterned cell-laden droplet networks. Hydrogels were selected to provide mechanical strength but that could also act as a cellularised scaffold, allowing for the culture of cells disposed within into microtissues. Development of microtissues into biologically relevant structures is highly dependent on the spatial arrangement of different cell types. In particular, it is desirable to combine a high resolution printing methodology with scaffold-assisted phase transfer to synthesize tissue samples with emergent biological properties.

Existing methods describe the phase transfer of single droplets or droplet clusters (~1-10) to give to giant unilamellar vesicles (GUV) (Pautot et al, *Proc. Natl. Acad. Sci. U.S.A.* 100, 10718-10721 (2003); Yamada et al, *Langmuir* 22, 9824-8 (2006); Walde et al, *Chembiochem* 11, 848-65 (2010); Abkarian et al, *Soft Matter* 7, 4610 (2011); Yanagisawa et al, *J. Am. Chem. Soc.* 133, 11774-9 (2011); Ito et al, *Soft Matter* 9, 9539 (2013)) and multi-compartmentalised vesicles. This was demonstrated by passing structures through the interface of a two-phase column of lipid-in-oil solution above aqueous solution (Elani, et al, *Chem. Sci.* 4, 3332 (2013)). The GUV formation methods used a spinning column to impart centrifugal force to aid phase transfer. The multi-compartmentalised vesicles method used a gravity-mediated approach, reliant on increasing the internal droplet density relative to the bulk phases to encourage droplet settling. Despite previous efforts, however, it remains challenging to phase transfer larger networks of lipid-stabilised droplets because any fabricated structure needs to not only overcome the surface tension of the oil-aqueous interface but also be fully coated with external lipid (to form an aqueous droplet network with internal droplet-droplet bilayers and external droplet-bulk aqueous bilayers).

There are only two literature examples of droplet network phase transfer (Elani, et al, *Chem. Sci.* 4, 3332 (2013) and Elani et al, *Nat. Commun.* 5, 1-5 (2014)). In those cases, the authors phase transferred dense sucrose-based droplets through a two phase column interface. The limitations of that research are as follows: phase transferred species are short-lived (generally an hour maximum); only sucrose droplets were demonstrated (which is not an ideal environment for cells); droplets were of large volume (ø≥500 μm i.e. ≥65 nL); networks were simple (composed of 2-8 droplets); and phase transfer occurred only 43% or 80% of the time (depending on the solution).

It is therefore an object of the invention to develop a process which allows the phase transfer of high resolution volumes of hydrogel (which may be cargo-laden) without loss of pattern fidelity.

SUMMARY OF THE INVENTION

In view of the above-described problems with prior art processes, the inventors have developed a technique to phase transfer a volume of a hydrogel (for instance a patterned droplet network laden with a cargo such as beads or biological cells, for instance as shown in FIGS. 2A-2D to 5A-5D) from a bulk hydrophobic phase into a bulk aqueous phase. This is achieved by using a multistep gelation-based methodology which results in minimal disruption to pattern fidelity.

The invention was developed by suspending beads or cells in a solution of a hydrogel compound, for instance an agarose-based solution, and 3D printing this as patterned droplet networks, which were subsequently gelled, wrapped in a secondary stabilising gel, and then phase transferred using a two-phase column. Essentially, the droplet network was converted into a gel scaffold, which then sank through an oil-aqueous interface. The process of the invention holds the patterned cargo in place by encasing within a solid gel, as shown by imaging before and after phase transfer (for instance FIGS. 2A-2D). The process also disrupts any internal lipids present as may be demonstrated by cell staining and proliferation of cells within the scaffold by the incorporation of cell dyes and cell nutrients into the bulk aqueous phase respectively. The transferred gelled assemblies contain greater internal structure than possible with a moulded scaffold (for cell based experiments).

Cell-laden scaffolds may be transferred by the process of the invention into an osmotically balanced culture medium and then cultured the cells for a number of days. The biological cells within such transferred networks have been shown to be viable, to proliferate and to retain their differentiating capacity within the scaffolds. Further advantages of the process of the invention are set out below.

The process of the invention is highly reproducible and has a high success rate. In particular, the hydrogel objects will most often phase transfer rather than rest on the oil-aqueous interface. This is due to the hydrogel-based gel being denser than the lower aqueous solution and hence it sinks by gravity. The phase transfer of mm-scale scaffolds (typically 1×1×0.4 mm$^3$) has been repeated numerous (n>100) times and it has been empirically noticed that ~90% of scaffolds transfer when placed in the column without further force, whilst ~10% of scaffolds need light mechanical perturbation by hand (i.e. the chamber slide is rotated in slow circular motion). In contrast Elani et al, *Chem. Sci.* 4, 3332 (2013) has a lower phase transfer success rate of 43%, which rose to 80% when vesicles were incorporated. The unsuccessful attempts have the droplet network rupture into the bulk aqueous phase during the phase transfer.

In the process of the invention, the volume of hydrogel (e.g. scaffold) is a solid gel and there is no risk of the volume of hydrogel solubilising or coalescing with the bulk phase. The scaffold can be used at room temperature and cell culture conditions without degrading. This has been demonstrated in numerous experiments as the inventors have regularly culture cells within scaffolds over 1 week. Elani et al, *Chem. Sci.* 4, 3332 (2013) shows phase structures which have an average lifetime of 60 min.

Unlike prior art processes, the structure does not need to be coated in a lipid bilayer and the two phase column doesn't have to be incubated such that a continuous lipid monolayer forms at the oil-aqueous interface. This means that the hydrogel objects tend to transfer within about 60 seconds. All other GUV and multicompartmentalised vesicle methods typically need to incubate the lipid monolayer for from 0.5 to 4.0 hours.

The process of the invention is compatible with volumes of hydrogel which are high order droplet networks. For instance, high order droplet networks containing hundreds of droplets (of ~1 nL volume) have been successfully converted into hydrogel scaffolds and phase transferred. The method is also compatible with large single droplets (of 200 nL volume). In contrast, the most complex droplet network phase transferred in Elani et al, *Chem. Sci.* 4, 3332 (2013) was a network of seven droplets.

It is possible to maintain high pattern fidelity with the process of the invention. The pattern of cargo disposed in a volume of hydrogel, for instance beads or cells in a droplet assembly, is conserved throughout the gelation steps and the final phase transfer step. The inventors have shown this by phase transferring scaffolds consisting of a bilayer of cell-type 1 next to cell-type 2 (for instance as shown in FIGS. 4A-4G).

Small molecules such as cell dyes and cell nutrients have been shown to penetrate the phase transferred volumes of hydrogel. Scaffolds laden with cells were successfully stained post phase transfer by live/dead staining protocols using calcein-AM and propidium iodide (at 5 μM absolute dye concentration). Also cells were cultured over 7 days, by incubating the samples in bulk culture medium, and showed proliferation, as there was insufficient nutrients in the scaffold and the build up of waste products the scaffold must have been permeable.

Hydrogels such as agarose used in the process of the invention are non-cytotoxic and cells within the transferred hydrogel object showed high viabilities post phase transfer of ≥80%, with the cells originally 90-100% viable prior to droplet network production.

The transferred hydrogel object typically does not inhibit normal biological activities, such as ability to differentiate, as shown by HEK-293T cell laden scaffold culture experiments. Cell-laden scaffolds were cultured over one week using optimised culture and scaffold handling conditions and an increase in the number of cells and the formation of unique 3D cell cluster morphologies which grow within the gel scaffold over time were observed. Immunocytochemistry staining was also performed (as shown in FIG. 5D), with seven day old HEK-293T scaffolds displaying 2.6±1.8% mitotic activity.

The invention therefore provides a process for producing a composition comprising an aqueous medium and, disposed in the aqueous medium, a first volume of a first hydrogel, which process comprises:

(i) providing a composition comprising a first hydrophobic medium and, disposed in the first hydrophobic medium, a first volume of a first hydrogel;
(ii) disposing a volume of an aqueous composition comprising a hydrogel compound around the first volume of the first hydrogel;
(iii) allowing the aqueous composition comprising the hydrogel compound to form a gel and thereby forming a hydrogel object, which hydrogel object comprises the first volume of the first hydrogel and a second volume of a second hydrogel, which second volume of the second hydrogel is disposed around the first volume of the first hydrogel; and
(iv) transferring the hydrogel object from the first hydrophobic medium to an aqueous medium and thereby producing the composition comprising the aqueous medium and, disposed in the aqueous medium, the first volume of the first hydrogel.

The invention further provides a hydrogel object, which hydrogel object comprises a first volume of a first hydrogel and a second volume of a second hydrogel, which second volume of the second hydrogel is disposed around the first volume of the first hydrogel, wherein the first volume of a first hydrogel comprises a droplet assembly comprising a plurality of droplets of the first hydrogel and each droplet of the first hydrogel comprises one or more cargo items disposed therein.

BRIEF DESCRIPTION OF THE FIGURES

FIGS. 1A-1C show a schematic diagram of the process of the invention. FIG. 1A shows gelation of a printed network to produce a gelled droplet assembly (i.e. the first volume of the first hydrogel). FIG. 1B shows gel coating of the gelled droplet assembly with an aqueous composition comprising a hydrogel compound and subsequent gelation to form a set coating of an exterior gel (i.e. a second volume of the second hydrogel) around the gelled droplet assembly (i.e. the first volume of the first hydrogel). This is the hydrogel object. FIG. 1C shows the phase transfer of the hydrogel object in an aqueous medium.

FIGS. 4A-4G show micrographs and fluorescence images of printed hydrogel scaffolds laden with biological cells patterned in a lamellar architecture before and after phase transfer.

DETAILED DESCRIPTION OF THE INVENTION

Figure 2A:
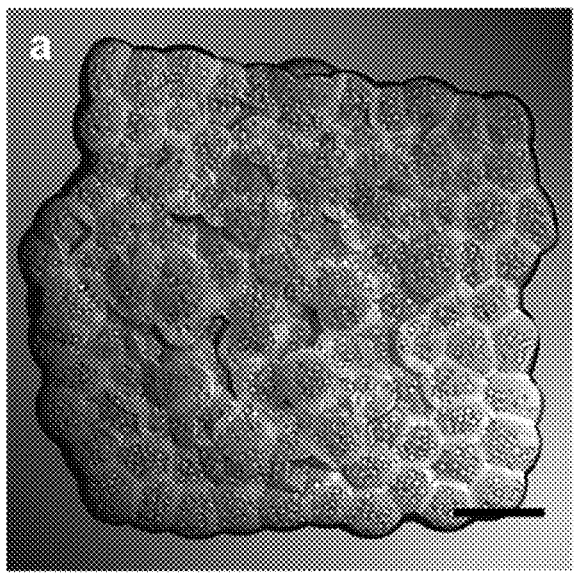
FIGS. 2A-2D show micrographs of the stages of the gel-wrapping and phase transfer of a cell-laden volume of a first hydrogel.

The invention provides a process for producing a composition comprising an aqueous medium and, disposed in the aqueous medium, a first volume of a first hydrogel, which process comprises:
(i) providing a composition comprising a first hydrophobic medium and, disposed in the first hydrophobic medium, a first volume of a first hydrogel;
(ii) disposing a volume of an aqueous composition comprising a hydrogel compound around the first volume of the first hydrogel;
(iii) allowing the aqueous composition comprising the hydrogel compound to form a gel and thereby forming a hydrogel object, which hydrogel object comprises the first volume of the first hydrogel and a second volume of a second hydrogel, which second volume of the second hydrogel is disposed around the first volume of the first hydrogel; and
(iv) transferring the hydrogel object from the first hydrophobic medium to an aqueous medium and thereby producing the composition comprising the aqueous medium and, disposed in the aqueous medium, the first volume of the first hydrogel.

A schematic diagram of the gel encapsulation and phase transfer of printed droplet networks containing cells (a.k.a. cell scaffolds) of the invention is shown in FIG. 1A. The printed network is first gelled within the print oil by cooling (4° C., 20 min). The lipid of the print oil is then diluted out, by repeated silicone oil washes, leaving the network free of an outer lipid coating. FIG. 1B Gel encapsulation of a printed network. The surface of the gel network is wetted with a pipetted agarose droplet. The agarose enveloped structure is then gelled within the oil by cooling (4° C., 20 min). FIG. 1C Phase transfer. The gelled encapsulated and gelled network is moved into the upper phase of a two-phase column of oil above culture medium and sinks through the interface. The oil is removed from the container, which is then topped up with additional culture medium and stored in a cell incubator.

A hydrogel compound is a compound such that an aqueous solution of the hydrogel compound is capable of gelling to form a hydrogel. Typically an aqueous medium comprising a hydrogel compound will gel to form a hydrogel when the temperature of the aqueous medium is reduced below a certain temperature (which will be the gelling temperature of the hydrogel compound in that aqueous medium). An aqueous composition comprising a hydrogel compound is not typically itself a gel but rather a free flowing liquid. It is only once such an aqueous composition comprising the hydrogel compound has gelled that the aqueous composition is a hydrogel. A gel may be defined as a "nonfluid colloidal network or polymer network that is expanded throughout its whole volume by a fluid". A hydrogel may be defined as "a gel in which the swelling agent (i.e. the fluid) is water".

The first volume of the first hydrogel typically comprises one or more cargo items disposed therein. The process of the invention allows for preservation of the pattern fidelity of cargo objects disposed in a volume of a first hydrogel during phase transfer.

A cargo item is any suitable item, particle or object which may be suspended in a hydrogel. For instance, the cargo items may be selected from plastic beads, nanoparticles, microparticles or biological cells. Typically, the one or more cargo items are one or more biological cells.

The term "biological cell", as used herein, is well known and refers to a cell comprising a cytoplasm (typically comprising organelles such as a nucleus or ribosomes) enclosed within a membrane. The biological cells may be prokaryotic or eukaryotic. The biological cells are typically eukaryotic. The biological cells may be naturally occurring or genetically (or otherwise) modified. Often, the biological cells are mammalian cells derived from mammalian tissue. For instance, the biological cells may be derived from primate tissue such as human or chimpanzee tissue.

In some embodiments, the one or more biological cells are selected from two or more different types of biological cells.

A type of a biological cell refers to the cell type of a biological cell taken from a particular species. For instance, typical examples of mammalian biological cell types include human embryonic kidney (HEK) cells, osteoblast cells, chrondrocyte cells and mesenchymal stem cells (MSCs). Cells may be differentiated cells or stem cells which may be multipotent or totipotent.

The one or more biological cells are typically mammalian cells. For instance, the one or more biological cells may be primate cells such as human cells.

Typically, if present, the one or more biological cells are disposed in the first volume of the first hydrogel at a concentration of from $10^4$ to $10^8$ cells per mL of first volume of the first hydrogel. For instance, the concentration of the biological cells disposed in the first volume of the first hydrogel may be from $10^5$ to $10^7$ cells per mL or from $10^6$ to $10^8$ cells per mL. Preferably the concentration of biological cells in the first volume of the first hydrogel is greater than or equal to $10^5$ cells per mL.

The first volume of a first hydrogel is typically obtained by gelling a volume of an aqueous composition (which may be referred to as an ink or a bioink). The volume of an ink or bioink may be produced by generating droplets of the ink or bioink in a hydrophobic medium. Prior to gelling, the ink or bioink typically comprises an aqueous solution of a hydrogel compound (the component which is gelled to form the hydrogel) and the one or more cargo items disposed therein (if present). The ink or bioink typically further comprises a culture medium, particularly if the cargo items are biological cells. As gelling usually only leads to a change in phase of the hydrogel compound to form a hydrogel, all of the components typically remain in the hydrogel.

The first volume of the first hydrogel further typically comprises a culture medium. A culture medium is any aqueous medium suitable for culturing biological cells and culture media are well known to the skilled person. The culture medium is typically an aqueous solution of one or more amino acids (for instance glutamine or a source thereof), one or more salts (for instance sodium chloride or sodium pyruvate), glucose, and one or more vitamins (for instance vitamins A, B, C or D). The culture medium may further comprise one or more antibiotics. Examples of antibiotics include penicillin and streptomycin.

In some embodiments the volume of the first hydrogel comprises: (a) a (gelled) hydrogel compound at a concentration of from 0.5 to 30.0 mg/mL; (b) a culture medium at a concentration of from 60.0 to 90.0 volume % and (c) optionally the one or more cargo items.

The first volume of the first hydrogel may be in any form. The first volume of the first hydrogel may be a single continuous volume of the first hydrogel which may be any shape, for instance substantially spherical or cuboidal. The first volume of the first hydrogel may comprise a plurality of sub-volumes of the first hydrogel which may have interfaces between them. Typically, the first volume of the first hydrogel comprises a droplet assembly comprising a plurality of droplets of the first hydrogel. The first volume of the first hydrogel may have a range of sizes. For instance, the greatest external dimension of the first volume of the first hydrogel may be from 1.0 mm to 10 cm or less than or equal to 1.0 mm. If an object has a largest external dimension of x, then the object can fit within a cube having a side length of x.

The term "droplet", as used herein, typically refers to any bound volume of a material (which may for instance be a liquid or a gel). The volume of a droplet is typically less than 1.0 mL, for instance less than 0.1 mL. For instance, a bound volume of a volume of a hydrogel having a volume of less than 500 nL is a droplet. When first generated, a droplet may be substantially spherical in character. However, once in contact with other droplets in the droplet assembly a droplet may adopt a range of shapes. Typically, a droplet has a sphericity (e.g. the ratio of the surface area of a sphere of the same volume as the droplet to the actual surface area of the droplet) of greater than or equal to 0.5, for instance greater than or equal to 0.6. Thus, the greatest external dimension of a droplet (e.g. length) is typically less than or equal to 2.0 times the smallest external dimension of a droplet (e.g. width). The term "droplet of a medium" is typically equivalent to the term "volume of a medium".

A droplet assembly is a collection of droplets, which is typically arranged in a three dimensional array. Typically in a droplet assembly, each droplet is in contact with at least one other droplet in the assembly. A "droplet assembly" may also be referred to as a "assembly of volumes [of the material comprised in the droplets]". A droplet assembly produced by the process of the invention may be of any size. For instance, the largest external dimension of a droplet assembly may be from 0.01 mm to 100.0 mm. The largest external dimension of the droplet assembly may, in some cases, be less than or equal to 10.0 mm, for instance less than or equal to 5.0 mm. A droplet assembly may also be referred to as a "scaffold".

The droplet assembly which may form the first volume of the first hydrogel typically comprises a plurality of droplets of the first hydrogel arranged in a three dimensional structure and wherein each droplet in the three dimensional structure contacts at least one other droplet in the three dimensional structure.

The droplet assembly typically comprises 50 or more droplets of the first hydrogel. For instance, the droplet assembly may comprise 100 or more droplets of the first hydrogel, or 500 or more droplets of the first hydrogel. The droplet assembly typically comprises one or more droplets having a volume of from 0.001 to 1000 nL, for instance from 0.001 to 100 nL. The volume of the one or more droplets may be from 0.1 nL to 500 nL or from 1.0 nL to 300 nL.

Typically, if two or more cell types are present in the droplet assembly, one or more of the droplets each comprises two or more biological cells disposed in the first volume of the first hydrogel, and the two or more biological cells are selected from two or more different types of biological cells. Thus, individual droplets may comprise two or more types of cell. Alternatively, different droplets may comprise different cell types allowing structural features containing different cell types to be incorporated into the droplet assembly. Thus, in some cases, the droplet assembly may comprise a first plurality of droplets, each of which droplets comprises one or more of a first type of biological cells disposed in the first volume of the first hydrogel, and a second plurality of droplets, each of which droplets comprises one or more of a second type of biological cells disposed in the first volume of the first hydrogel.

The first hydrogel typically comprises a hydrogel compound which is polymeric. For instance, the first hydrogel may comprise a gelled hydrogel compound which is a polysaccharide, a polyvinyl alcohol, a polyacrylate, a polymer comprising a number of hydrophobic groups or a derivative thereof. The first hydrogel typically comprises a polysaccharide. Examples of polysaccharide hydrogel compounds include agarose, methylcellulose and hyaluronan. Preferably, the first hydrogel comprises agarose. The first hydrogel typically has a gelling temperature of less than 20° C. The gelling temperature may be as measured for an aqueous solution of the hydrogel compound with a concentration of 10 mg/mL.

The concentration of the hydrogel compound in the first volume of the first hydrogel is typically from 0.01 mg/mL to 500.0 mg/mL. For instance, the concentration of the hydrogel compound in the first volume of the first hydrogel may be from 0.1 mg/mL to 100.0 mg/mL, or from 0.5 mg/mL to 30.0 mg/mL. The concentration of the hydrogel compound may for example be from 10 to 13 mg/mL.

A hydrophobic medium is typically a hydrophobic liquid, for instance a liquid that is not substantially miscible with water (e.g. less than 2 wt % of the hydrophobic medium mixes with water). The first hydrophobic medium may be any hydrophobic medium. For instance, the first hydrophobic medium may comprise an organic compound. Typically, the first hydrophobic medium comprises a hydrocarbon compound. Often, the first hydrophobic medium comprises a hydrocarbon compound and/or a silicone oil.

A hydrocarbon compound is a compound comprising only carbon and hydrogen atoms. Examples of hydrogen compounds include $C_4$ to $C_{20}$ alkanes (for instance straight chain alkanes having from 6 to 18 carbon atoms) and $C_5$ to $C_{10}$ cycloalkanes (for instance cyclopentane or cyclohexane). Preferably, the hydrocarbon compound is a $C_8$ to $C_{16}$ alkane, for instance octane, nonane, decane, undecane or dodecane. Preferable, the hydrocarbon compound is undecane.

A silicone oil is an oil comprising a polymeric compound which comprises one or more siloxane groups. For instance, a silicone oil is typically a polymerized siloxane with organic side chains. For instance the silicone oil may comprise polydimethylsiloxane, polyethylmethylsiloxane or polydiethylsiloxane.

The first hydrophobic medium may for instance comprise a mixture of a hydrocarbon and a silicone oil in a ratio (hydrocarbon):(silicone oil) of from 50:50 to 80:20 by volume. Preferably, the ratio is from 60:40 to 70:30 by volume. The first hydrophobic medium may be a mixture of undecane and silicone oil in a ratio of from 60:40 to 70:30 by volume.

The volume of the first hydrophobic medium is typically from 0.01 mL to 100.0 mL, for instance from Typically, the first hydrophobic medium comprises a very low concentration of amphipathic compounds, preferably substantially no amphipathic compounds. A low or zero level of amphipathic compounds in the first hydrophobic medium means that any amphipathic compounds in the first volume of the first hydrogel are removed. Typically, the first hydrophobic medium comprises one or more amphipathic compounds at a total concentration of less than or equal to 0.1 mM, preferably at a total concentration of less than or equal to 0.05 mM. For instance, the first hydrophobic medium may comprise one or more amphipathic compounds at a total concentration of less than or equal to 0.02 mM.

An amphipathic compound is a compound comprising both hydrophilic groups and lipophilic groups (e.g. hydrophobic groups). Amphipathic molecules are typically able to form bilayers and micelles. Amphipathic molecules are well known to the skilled person. Examples of amphipathic compounds include lipids such as triglycerides, fatty acids and phospholipids. Typically, the one or more amphipathic compounds are selected from phospholipids. A phospholipid is compound comprising a glycerol molecule substituted with a phosphate group and one or more fatty acid groups. The one or more amphipathic compounds may be phosphocholine lipids.

In the process of the invention, a volume of an aqueous composition is disposed around the first volume of the first hydrogel. "Disposing around" is typically equivalent to "disposing on" since a volume of a liquid within a hydrophobic medium will spontaneously coat another hydrophilic object (i.e. the first volume of the first hydrogel). The volume of the aqueous composition coats the first volume of the first hydrogel and once the aqueous composition is gelled, this provides a second volume of a second hydrogel which acts as a protective layer around the first volume of the first hydrogel which assists in maintaining the structure and any pattern fidelity within the first volume of a first hydrogel.

The hydrogel object typically comprises a layer of the second hydrogel disposed on the surface of the first volume of the first hydrogel. The layer of the second hydrogel typically covers greater than or equal to 80% of the surface area of the first volume of the first hydrogel. The second hydrogel may for instance coat all of the surface of the first volume of the first hydrogel. The thickness of the layer of the second hydrogel may be greater than or equal to 0.01 mm, for instance greater than or equal to 0.1 mm. Typically, the thickness of the layer of the second hydrogel is from 1.0 to 200 µm, for instance from 45 to 85 µm.

Formation of the second volume of the second hydrogel around the first volume of the first hydrogel typically comprises first forming a volume of an aqueous composition comprising a hydrogel compound around the first volume of the first hydrogel which can then be gelled to form the second volume of the second hydrogel. The volume of an aqueous composition comprising a hydrogel compound around the first volume of the first hydrogel can be formed by a droplet of the aqueous composition spontaneously wetting the first volume of a first hydrogel. A low concentration of amphipathic compounds in the hydrophobic medium encourages wetting.

Typically, disposing a volume of an aqueous composition comprising a hydrogel compound around the first volume of the first hydrogel comprises: generating a droplet of the aqueous composition in the first hydrophobic medium; and contacting the droplet of the aqueous composition with the first volume of the first hydrogel. Once the droplet of the aqueous composition contacts the first volume of the first hydrogel it will typically spontaneously wet and coat the first volume of the first hydrogel. The droplet of the aqueous composition may be generated simultaneously with contacting the first volume of the first hydrogel.

The hydrogel compound in the aqueous composition is typically a polymeric compound, for instance a polysaccharide, a polyvinyl alcohol, a polyacrylate, a polymer comprising a number of hydrophobic groups or a derivative thereof. The hydrogel compound is typically a polysaccharide, for instance agarose, methylcellulose and hyaluronan. Preferably, the hydrogel compound is agarose. The aqueous composition comprising the hydrogel compound typically has a gelling temperature of less than 20° C.

The concentration of the hydrogel compound in the aqueous composition is typically from 0.01 mg/mL to 500.0 mg/mL. For instance, the concentration of the hydrogel compound in the aqueous composition may be from 0.1 mg/mL to 100.0 mg/mL, or from 0.5 mg/mL to 30.0 mg/mL. For instance, the aqueous composition may comprise the hydrogel compound at a concentration of from 1.0 to 20 mg/mL. Preferably, the aqueous composition comprises agarose at a concentration of from 8.0 mg/mL to 20.0 mg/mL.

The aqueous composition may be any liquid medium comprising water. Typically, the aqueous composition is a composition comprising greater than or equal to 80 wt % water or greater than or equal to 90 wt % by water. The aqueous composition comprising a hydrogel compound typically comprises the hydrogel compound dissolved in water.

The total volume of the aqueous composition and the volume of first hydrogel is typically greater than or equal to 100 nL. Preferably, the total volume is greater than or equal to 1000 nL.

The second hydrogel may be the same as or different from the first hydrogel. Typically, both the first and second hydrogels comprise agarose.

Allowing the aqueous composition comprising the hydrogel compound to form a gel typically comprises cooling the aqueous composition or exposing the aqueous composition to a compound or electromagnetic radiation (for instance UV light) which causes gelling. Allowing the aqueous composition comprising the hydrogel compound to form a gel typically comprises cooling the volume of the aqueous composition comprising the hydrogel compound to a temperature of less than or equal to 20.0° C., for instance less than or equal to 10.0° C.

Once the aqueous composition has gelled to form the second volume of the second hydrogel, the hydrogel object and at least part of the first hydrophobic medium is typically moved to a receptacle in which the phase transfer of the hydrogel object from the first hydrophobic medium to the aqueous medium can occur. Moving the hydrogel object and at least part of the first hydrophobic medium to the receptacle may for instance comprise using a pipette to move the hydrogel object. The first volume of the first hydrogel is typically moved to a second hydrophobic medium before being transferred to an aqueous medium. The receptacle is typically a column comprising two phases, a first phase and a second phase, as discussed below.

Transferring the hydrogel object from the first hydrophobic medium to an aqueous medium typically comprises allowing the hydrogel object to move from a second hydrophobic medium into an aqueous medium. Allowing the hydrogel object to move includes either applying a force to the hydrogel object to cause it to move and also allowing the hydrogel object to move under its own force.

The second hydrophobic medium is typically the hydrophobic phase in the phase transfer step in the process of the invention. Thus, the hydrogel object is formed in the first hydrophobic medium as described above. The hydrogel object is then moved into a second hydrophobic medium (which is typically a phase in a phase transfer column), optionally along with at least part of the first hydrophobic medium, for instance using a pipette. It is then from this second hydrophobic medium that the hydrogel object is transferred to the aqueous medium.

The second hydrophobic medium may be the same as, or different from, the first hydrophobic medium. Typically, the second hydrophobic medium comprises a hydrocarbon compound and/or a mineral oil. Examples of hydrogen compounds include $C_4$ to $C_{20}$ alkanes (for instance straight chain alkanes having from 10 to 18 carbon atoms) and $C_5$ to $C_{10}$ cycloalkanes (for instance cyclopentane or cyclohexane). Preferably, the hydrocarbon compound is a $C_{10}$ to $C_{18}$ alkane, for instance decane, undecane, dodecane, tridecane, tetradecane, pentadecane, hexadecane and heptadecane. Preferable, the hydrocarbon compound is hexadecane. The term mineral oil is well known to the skilled person. Typically, the mineral oil comprises one or more alkanes and one or more cycloalkanes. The mineral oil may for instance comprise one or more straight chain alkanes having from 8 to 16 carbon atoms. The density of the mineral oil is typically from 0.7 to 0.9 g/cm$^3$ at 25° C. Preferably, the second hydrophobic medium comprises hexadecane and mineral oil. The second hydrophobic medium typically comprises hexadecane and mineral oil at a volume ratio of from 1:1 to 5:1 of (hexadecane):(mineral oil).

Transferring the second volume of the second hydrogel comprising the first volume of the first hydrogel from the first hydrophobic medium to an aqueous medium comprises passing the hydrogel object through a first phase, which is a second hydrophobic medium, and into a second phase, which is an aqueous medium, and which second phase is in contact with the first phase. The first phase and second phase are typically in a phase transfer column. Thus, the first phase is less dense than the second phase at the temperature of the system. The first phase is located above the second phase.

The first phase typically has a lower density than the second phase and is disposed on the second phase, and passing the hydrogel object through the first phase and into the second phase comprises allowing the hydrogel object to fall through the first phase and into the second phase under the influence of gravity. In some cases, it may be necessary to agitate the first and second phases to cause the hydrogel object to fall through the phase boundary.

The aqueous medium is typically an aqueous medium suitable for culturing any biological cells disposed in the first volume of the first hydrogel. The aqueous medium typically comprises a culture medium. The first volume of the first hydrogel may therefore further comprise one or more biological cells disposed therein and the process may further comprise a step of culturing the one or more biological cells.

Formation of the first volume of the first hydrogel in the first hydrophobic medium often comprises generation of droplets of a precursor to the first hydrogel in an amphipathic molecule-containing hydrophobic medium and subsequently replacing the amphipathic molecule-containing hydrophobic medium with the first hydrophobic medium (which does not typically comprise amphipathic molecules). While amphipathic molecules may aid formation of the first volume of the first hydrogel, they are not typically required thereafter.

Thus, in some embodiments, the process further comprises, prior to step (i), the steps of: (a) providing a composition comprising an amphipathic molecule-containing hydrophobic medium with the first volume of the first hydrogel disposed therein; and (b) adding the first hydrophobic medium to the amphipathic molecule-containing hydrophobic medium, and optionally replacing at least part of the amphipathic molecule-containing hydrophobic medium with the first hydrophobic medium. Replacing at least part of the amphipathic molecule-containing hydrophobic medium with the first hydrophobic medium can remove the amphipathic molecules from the first volume of the first hydrogel by reducing the concentration of the amphipathic molecules in the hydrophobic medium surrounding the first hydrogel and allowing the amphipathic molecules to diffuse out. Replacing at least part of the amphipathic molecule-containing hydrophobic medium with the first hydrophobic medium may be done repeatedly, for instance two or three times. Replacing at least part of the amphipathic molecule-containing hydrophobic medium with the first hydrophobic medium is typically repeated until the concentration of amphipathic molecules in the hydrophobic media surrounding the first volume of the first hydrogel is less than or equal to 0.1 mM, or less than or equal to 0.02 mM.

Typically, in the step prior to step (i), the first volume of the first hydrogel disposed in the amphipathic molecule-containing hydrophobic medium comprises one or more droplets of the first hydrogel, each of which one or more droplets of the first hydrogel comprises an outer layer of amphipathic molecules.

The invention also provides a composition comprising an aqueous medium and, disposed in the aqueous medium, a first volume of a first hydrogel, which composition is obtainable from a process as defined herein.

The invention also provides a process for producing a first volume of a first hydrogel, which process comprises: (i) producing a composition comprising an aqueous medium and, disposed in the aqueous medium, a first volume of a first hydrogel by a process as defined herein; and (ii) isolating the first volume of a first hydrogel. Isolating the first volume of the first hydrogel may, for instance, comprise removing the aqueous medium. The first volume of the first hydrogel is then isolated, although typically still disposed within the hydrogel object. The second volume of the second hydrogel typically allows for nutrients and other molecules to pass from the first volume of the first hydrogel to the exterior of the hydrogel object via the second volume of the second hydrogel.

The invention also provides a first volume of a first hydrogel, which first volume of a first hydrogel is obtainable by a process as defined herein.

The invention also provides a process for producing tissue-like material, which process comprises a step of carrying out a process as defined herein. The process typically further comprises additional steps such as culturing the hydrogel object. The invention also provides a tissue-like material, which tissue-like material is obtainable by a process as defined herein.

The invention provides a hydrogel object, which hydrogel object comprises a first volume of a first hydrogel and a second volume of a second hydrogel, which second volume of the second hydrogel is disposed around the first volume of the first hydrogel, wherein the first volume of a first hydrogel comprises a droplet assembly comprising a plurality of droplets of the first hydrogel and each droplet of the first hydrogel comprises one or more cargo items disposed therein. The hydrogel object may be as further defined herein. The first volume of a first hydrogel and the second volume of the second hydrogel may be as defined herein.

Preferably, the one or more cargo items are one or more biological cells.

The invention also provides a composition comprising an aqueous medium and, disposed in the aqueous medium, a hydrogel object as defined herein.

The invention will be described further in the following Examples.

Examples

Summary

Cell-laden droplet assemblies (scaffolds) were produced by 3D patterning a cell-laden bioink as a high cell density and high resolution droplet network, which was subsequently gelled, gel encapsulated and then phase transferred into bulk culture medium. The steps involved are: (i) creating the scaffold solution; (ii) re-suspending harvested cells in the scaffold solution as a bioink; (iii) 3D droplet printing of the bioink into droplet networks; (iv) gelation and phase transfer of the cell-scaffold. The cell scaffolds can then be cultured over a week or longer forming dense microtissues which show biological activity.

The steps are briefly described below and further detail can be found in the experimental details section.

Scaffold Solution:

The scaffold solution is made of a hydrogel in a bulk cell culture medium with additional cell specific supplements where required. The hydrogel used was an ultra-low gelling temperature agarose, as bioinks composed of this could be printed as a sol (or pre-gel liquid) at room temperature and then gelled at 4° C. within a refrigerator. Supplements used were FMOC-dipeptides (FMOC-IG and FMOC-FF, where I is isoleucine, G is glycine and F is phenylalanine), which acted as both a network stabilising agent (i.e. prevented coalescence) and increased droplet-droplet adhesion within a network. Extracellular matrix proteins (ECM) were also used to supplement the bioink, and these were either collagen type I, fibronectin or laminin, as these offered adhesion sites for the cells. It was empirically noticed that these ECMs encourage cell growth within the scaffold. In the majority of experiments the ECM supplement used was collagen type I.

Resuspension of Harvested Cells as Bioink:

Cells grown by standard 2D culture methods were harvested from culture flasks and centrifuged to give a pellet. This cell pellet was then re-suspended in the scaffold solution at a typical cell density of $15 \times 10^6$ cells/mL. Cells were re-suspended at this high density as it was found the cells would form multiple contacts with one another in the printed structure and would proliferate better than other observed lower cell density scaffolds. Mammalian cell lines used included: HEK-293T, HEK-293/YFP, HEK-293/CFP, ovine mesenchymal stem cells (oMSCs), oMSC-derived-osteoblasts and murine chondrocytes.

3D Bioprinting of the Droplet Networks:

A 3D droplet printer was used to print the bioink as cell-laden droplet networks. The printing was done by first lowering the bioink loaded print nozzle into a bath of lipid-in-oil solution, and finding print parameters that reproducibly form droplets. These conditions could then be used to automate printing of 3D droplet networks by successive layering of spatially assigned droplets (based on digital "printing maps"). The optimised printing oil used was a 65:35 v:v mix of undecane:silicone oil containing 1.2 mM DPhPC. This oil was designed to allow ideal printing (optimised sinking speed) and the DPhPC is used as it forms stable bilayers. It was observed for bioink printed networks that the structure almost never showed any droplet-droplet coalescences, and formed a tightly packed structure.

Network Gelation and Gel Coating (Phase Transfer Prep):

The printed network was gelled by cooling to 4° C. for 20-25 min. Gelled cargo-laden networks showed no loss in pattern fidelity. The structure was coated in a small volume of agarose hydrogel (0.2-0.4 nL). First the print oil was exchanged for silicone oil and then a droplet of agarose solution was coalesced with the printed structure. Oil exchange was used to remove lipids from the printed network, allowing coalescence rather than droplet interface bilayer formation to occur. The coated structure was then be gelled (4° C. for 20-25 min). The wrapping step is key as it holds the gel droplets together and prevents shape distortion during phase transfer.

Phase Transfer of Cell Scaffold:

Structures were phase transferred by passing through an oil-culture medium interface, in this case a two phase column of 3:1 v:v mix of hexadecane to mineral oil above cell culture medium. The cell scaffold were micropipette transferred to the upper oil phase and passed through the interface by gravity. After phase transfer the oil was removed and the cell scaffold was stored in a cell incubator and cultured over a week.

The oil mix was found by empirically testing different oil and lipid combinations based on previously published phase transfer experiments. This oil combination was found to allow the network to gently sink through the interface with minimal oil contamination.

Experimental Details:

Scaffold Solution:

This section goes through the scaffold solutions (also referred to as bioinks) that were used to fabricate phase transferrable scaffolds. First the bioink handling and compositions are explained and then how to make scaffold supplements.

Solution Preparation Overview

All scaffold solutions 1-3 (SS1-3) (see Table 1) were produced in the same manner: i.e. the bulk phase of the scaffold was first prepared as a liquid or pre-gel solution, then scaffold supplements were added and finally the cells re-suspended at the desired density.

To minimise bacterial infection, various steps were taken to sterilise the scaffold solution. However, each bioink production used aseptic techniques and bioink processing where possible and was performed in a laminar flow biosafety cabinet. The resulting cell-laden bioinks were stored in a $CO_2$ incubator [Midi 40, Thermoscientific] at 37° C. with 5% $CO_2$ prior to use. Bioinks were generally printed within 30 min of production, but have been stored up to 4 h prior to use.

Agarose-Based Solutions (SS1-SS3)

All agarose-based scaffold solutions consisted of ultralow gelling point agarose with or without scaffold supplements. These solutions were prepared as a liquid and kept above the agarose gel melting temperature (i.e. ~50° C.) until the addition of ECM protein or cells, at which point the solution was kept at 37° C. Prior to the addition of cells, the solutions were UV irradiated, each for 15 min at 365 nm wavelength beneath an UV LED [Eclipse—M365L2-C5, Nikon] which was controlled by a LED driver [LEDD1B, Thorlabs] set to half power. All agarose-based scaffold solutions were used on the day of creation and not stored for future use.

SS1 & SS2: Agarose with FMOC-XX

The FMOC-dipeptide supplemented agarose solutions were prepared as an 8:1 V:V mix of 13-15 mg/mL agarose with 10 mM FMOC-XX respectively. The original agarose solution (SS1) was undiluted, whilst the diluted agarose solution (SS2) also contained 10% v/v PBS. UV treatment was applied prior to cell addition for scaffold solution 1 and prior to PBS addition for scaffold solution 2.

The final composition of scaffold solution 1 was: 11.6-13.3 mg/mL agarose and 1.1 mM FMOC-XX, in 88.9% base medium and 11.1% ultrapure water.

Whereas the final composition of scaffold solution 2 was: 10.4-12.0 mg/mL agarose and 1.0 mM FMOC-XX, in 80% base medium, 10% ultrapure water and 10% PBS.

SS3: Agarose with FMOC-XX and ECM Supplements

Additional bioinks involved supplementing scaffold solution 2 with ECM proteins (either collagen, fibronectin or laminin) at varied concentrations. The preparation was the same as scaffold solution 2, except, to the UV sterilised agarose with FMOC-XX solution, ECM protein in PBS was initially added at the desired concentration, followed by just PBS to give a 10% v/v PBS fraction. The scaffold solution at this stage was sonicated (5 min, 40 kHz) in a 2800 ultrasonic cleaner [Branson]. The ECM proteins were supplemented between the concentration ranges of: 3.5-300 µg/mL for collagen; and 0.5-20 µg/mL for fibronectin and laminin. A supplement of 15 µg/mL collagen was chosen as a standard for microtissue growth.

Hence the final composition for the standard scaffold solution 3 was: 10.4-12.0 mg/mL agarose, 1.0 mM FMOC-XX and 15 µg/mL collagen, in 80% base medium, 10% ultrapure water and 10% PBS.

Scaffold Supplement Preparation 10 mM FMOC-IG & 10 mM FMOC FF Solutions 10 mM solutions of FMOC-isoleucine-glycine (FMOC-IG) and FMOC-phenylalanine-phenylalanine (FMOC-FF), were prepared from powder aliquots stored at −20° C., and allowed to warm to room temperature. FMOC-IG (16 mg) and FMOC-FF (12 mg) were separately dissolved in, ultrapure water (1.5 mL) with 1 M NaOH (10-20 µL), and left to stir overnight. The partially solubilised FMOC solution was sonicated (20 min, 37° C., 40 kHz) in a Branson 2800 ultrasonic cleaner, pH corrected with 0.1 mM NaOH to either 8.50 (FMOC-IG) and 10.50 (FMOC-FF), and then diluted to 3 mL total volume with ultrapure water. FMOC-IG and FMOC-FF were used within a week and pH corrected if necessary before use.

10 mM FMOC-XX Solution

An FMOC-XX solution was an equal molar ratio solution of FMOC-IG and FMOC-FF. For a 10 mM FMOC-XX solution, 10 mM FMOC-FF and 10 mM FMOC-IG were mixed as a 1:1 V:V solution and then sonicated (40 kHz). FMOC-XX was made fresh on the day of use.

Agarose Solutions

Ultralow gelling point agarose [A5030] was used to make the 13-15 mg/mL agarose solution. Typically agarose powder and base medium were warmed in a water bath (65° C.). Warmed agarose powder (typically ~12 mg) was dissolved in warmed base medium (typically ~0.8 mL). To aid solvation, the solution was vortex mixed and, optionally, mechanically perturbed by micropipette aspiration or sonicated (40 kHz). The agarose solution once made was left in a water bath (65° C.). The base medium was either, Opti-MEM® for HEK-293 derivative cell lines or DMEM-ITS for oMSC, osteoblasts and chondrocytes.

ECM Protein Supplements

The ECM proteins were prepared by diluting from stock concentrations into an active gel form i.e. the working solution. Stock solutions of the ECM proteins were 5.0 mg/mL bovine collagen I, 1.0 mg/mL natural mouse laminin, and 1.0 mg/mL human fibronectin, and stored as aliquots at either, 4° C. (collagen) or −20° C. (laminin and fibronectin). The collagen I gel working solution (3.0 mg/mL) was prepared by mixing ice-cold reagents in the order: collagen I stock (50 µL), 10× concentrate PBS (8.3 µL), 1 N NaOH (1.3 µL), and ultrapure water (23.8 µL). Laminin and fibronectin working solutions (0.1 mg/mL) were made by diluting the respective stock solutions in PBS (typically 10 µL protein stock with 90 µL PBS). All ECM protein-working solutions were prepared just before their addition to the bioink, in a laminar flow biological safety cabinet.

TABLE 1

Agarose-based bioink compositions.

| # | Scaffold Solution Type | Typical Scaffold Solution Composition | Cell ρ used (cells/mL) | Scaffold Phase Transferrable? |
|---|---|---|---|---|
| SS1 | Agarose with FMOC-XX (original) | 89% v/v: 13-15 mg/mL agarose in Opti-MEM ® or DMEM-ITS<br>11% v/v: 10 mM FMOC-XX in ultrapure water | $5\text{-}15 \times 10^6$ | Yes |
| SS2 | Agarose with FMOC-XX (diluted) | 80% v/v: 13-15 mg/mL agarose in Opti-MEM ® or DMEM-ITS<br>10% v/v: 10 mM FMOC-XX in ultrapure water<br>10% v/v: PBS | $1\text{-}15 \times 10^6$ | Yes |
| SS3 | Agarose, FMOC-XX with ECM protein | 80% v/v: 13-15 mg/mL agarose in Opti-MEM ® or DMEM-ITS<br>10% v/v: 10 mM FMOC-XX in ultrapure water<br>10% v/v: ECM protein dissolved in PBS | $5\text{-}15 \times 10^6$ | Yes |

Resuspension of Harvested Cells as Bioink:

Cells were harvested and mixed into scaffold solutions as follows. For HEK-293T i.e. non adherent cells, a confluent T25 flask culture was resuspended in Opti-MEM® (5 mL), an aliquot of this (typically 1-2 mL) was centrifuged (3-5 min, 300-500×G) in a 5702 centrifuge [Eppendorf] and the resulting pellet was resuspended in the scaffold solution at the desired cell density. For a typical resuspension, 100-200 µL of scaffold solution was mixed with cells to give a $15 \times 10^6$ cells/mL solution. Whereas, for adherent cell lines such as HEK-293/YFP, before an aliquot of cell solution was obtained, the culture was first trypsinised, and then resuspended in Opti-MEM® (31985-062) post centrifugation. When MSC, osteoblast or chondrocyte bioinks were prepared and the cells were re-suspended in DMEM-ITS medium instead of Opti-MEM®.

To re-suspend the cells at the desired density from a cell suspension aliquot, the cell density of the aliquot was first determined and the resuspension volume calculated using Equation 3. This equation derives from the total cell number ($n_{cells}$) of a solution being equal to cell density ($\rho_{cells}$, in cells/mL) multiplied by volume ($V_{cells}$, in mL) Equation 1. For a resuspension, the total number of cells doesn't change, hence the cell number formula can used to equate the original and final volume solutions as Equation 2, which can be rearranged as Equation 3.

$$n_{cells} = \rho_{cells} \times V_{cells} \quad \text{Equation 1}$$

$$\rho_{initial} \times V_{initial} = \rho_{final} \times V_{final} \quad \text{Equation 2}$$

$$\frac{\rho_{initial}}{\rho_{final}} \times V_{initial} = V_{final} \quad \text{Equation 3}$$

The standard way to determine the density of the cell aliquot was to mix 100 µL:100 µL cell aliquot to trypan blue solution (dead cells only, stained dark blue) to produce a count solution. This solution (2×10 µL) was added to a disposable haemocytometer chip which is read by an automated cell counter [II FL, Countess] on either side of the chip to give two sets of values. The automated cell counter gives the live cell density, dead cell density and total cell density. The average of the two live cell density counts was used as the value for the initial cell density, and subsequently used in order to calculate the resuspension/final volume using Equation 3.

3D Bioprinting of the Droplet Networks:

Droplet Printer Overview

A description of an example of an apparatus for generating droplets (e.g. a 3D-printer of droplet networks) can be found in Villar et al, Science 340, 48-52 (2013). In brief, the droplet generator (which may be referred to as "piezo") comprised a piezoelectric disc which seals the back of an aqueous chamber with a protruding tapered capillary. The piezo can eject droplets from the nozzle upon application of a square-wave voltage pulse when the tip is submerged in a bulk hydrophobic medium such as a lipid-in-oil solution. An electronic micromanipulator was used to move the printing stage, e.g. an oil container, in three dimensions. This in combination with lab-designed printing software that interprets digital "printing maps" and automates droplet ejection, allowed the constructing of 3D droplet networks by successive layering of spatially assigned droplets.

Printer Preparation

Before printing, the piezo's aqueous chamber, printing oil container, and other print items, were thoroughly cleaned with ultrapure water and ethanol, then dried under $N_{2\,(g)}$. On the day of use, capillaries were flushed with ultrapure water, ethanol and isopropanol and then dried under $N_{2\,(g)}$. Cleaned capillaries were subsequently vacuum-sealed in a plasma cleaner [Femto version A, Diener Electronic] and treated with oxygen plasma (8 min, 5-10 SCCM). With the instrument cleaned, the piezo was filled with ultrapure water and the capillary inserted.

In between each newly loaded bioink, the capillary was cleaned by soaking in Virkon and then 8 M NaOH, and the aqueous chamber was replenished with lost water. For agarose-based bioinks the capillary was also cleaned by soaking in pure water at 65° C.

Printed Cell-Laden Droplet Networks

Cell laden scaffolds were printed into 65:35 v:v mix of (undecane):(silicone oil) containing 1.2 mM DPhPC with an agarose-based scaffold solutions containing cells (i.e. a bioink). The standard print protocol now follows.

The bioink was vortex mixed and an aliquot (10 µL) was placed in the printer loading well array alongside hexadecane (8 µL). Hexadecane (~1 µL) was first suction loaded into the printer nozzle followed by the bioink (1-6 µL). For agarose-based bioinks, the outside tip of the glass capillary was subsequently wiped with a lens tissue soaked in pure water.

Once the capillary was submerged into the print oil (usually 200 µL), the piezo was continually fired with varied voltage pulses until conditions were found for the reproducible ejection of singlet droplets, ideally of uniform size. Typical tuned pulse parameters were 50-350 µs pulse-width with voltages of 40-63 V.

The tuned pulse could be used to automate print cell-laden droplet networks. Typically, the voltage of this print pulse was gradually increased throughout a print session of multiple networks to keep consistent droplet production. Generally, multiple networks were successively printed within the same print chamber, with the last network left to stand for 5 min before moving. Information on the bioink print order and print parameters are found below for the different network types.

Single Cell-Type Scaffolds

Cell scaffolds of a single cell-type were mainly printed as 2-4 layer droplet square cuboids with horizontal map dimensions (x×y pixels) of 7×9 or 7×8. For scaffolds (i.e. droplet assemblies) to be phased transferred, 4 layers was the usual thickness. Such scaffolds are shown in FIGS. 2A-2D and 3A-3F.

Lamellar Scaffolds (Two Cell-Types)

For all junction scaffolds, cell-laden bioink with or without collagen as printed using a single droplet generator to print cell-type 1 first, then cell-type 2 after nozzle cleaning and bioink loading. Each junction consisted of a wider basement droplet square cuboid (cell-type 1), on top of which, was a centrally aligned narrower droplet square cuboid (cell-type 2). A lamellar scaffold is shown in FIGS. 4A-4G.

In all instances the junction networks were printed as follows, the lower droplet sheet was printed as a full map (i.e. a map where droplets were ejected at each pixel) for 3-4 layers and then sometimes the structures edges were flattened by printing a hollow map (i.e. a map where droplets were ejected only at the border of the map) for two further layers on top. The upper layer was printed similarly: a full map for 3-4 layers then sometimes a hollow map for two layers. The specific map sizes and number of layers printed for each junction are summarised in Table 2.

TABLE 2

Print details for the cell junction production. Each junction print is listed with bioink cell density, and the map dimensions (horizontal pixels x × y by vertical pixels z) for the upper and lower layers. Non-fluorescent cells were stained with red CMPTX (RC) or deep red (DR) cellTracker™ dye. The chondrocyte-osteoblast junction was printed at two separate occasions (listed in the order they were printed).

| | | | Lower Print Dimensions | | Upper Print Dimensions | |
|---|---|---|---|---|---|---|
| Printed Junction | Lower Cell $\rho$ (cells/mL) | Upper Cell $\rho$ (cells/mL) | Full Map ((x × y) × z) | Hollow Map ((x × y) × z) | Full Map ((x × y) × z) | Hollow Map ((x × y) × z) |
| chondrocyte (DR) below osteoblasts (RC) [1] | $3 \times 10^6$ | $1 \times 10^6$ | $(7 \times 9) \times 3$ | N/A | $(6 \times 8) \times 4$ | N/A |
| chondrocyte (DR) below osteoblasts (RC) [2] | $6 \times 10^6$ | $10 \times 10^6$ | $(7 \times 9) \times 4$ | $(7 \times 8) \times 2$ | $(6 \times 7) \times 4$ | N/A |
| HEK-293/YFP below HEK-293/CFP (DR) | $10 \times 10^6$ | $9 \times 10^6$ | $(7 \times 9) \times 3$ | $(7 \times 9) \times 2$ | $(6 \times 7) \times 4$ | N/A |
| HEK-293T (RC) below HEK-293T (DR) | $12 \times 10^6$ | $14 \times 10^6$ | $(7 \times 8) \times 3$ | $(7 \times 9) \times 2$ | $(6 \times 7) \times 3$ | $(6 \times 7) \times 2$ |

Printed Scaffold Gelation and Gel Encapsulation:

The steps of the gelation and gel encapsulation of printed scaffold can be seen schematically in FIGS. 1A-1C. These steps were performed aseptically where possible, with scaffolds under oil treated as aseptic.

Scaffold Gelation

Printed scaffolds comprising either SS1, SS2 or SS3 bound in standard bioink print oil were left to rest (5 min) post print. The scaffolds were then gelled in a fridge (4° C., 20-25 min). Gelled networks were either used straight away or stored in a hydration chamber.

Gel Coating of Scaffold

The oil surrounding the gelled networks was reduced to ~150 μL. Silicone oil AR20 (200 μL) was gently added to the corner of the cuvette, and then mixed oil (200 μL) was removed from the diagonally opposite corner. This silicone oil addition and mixed oil removal step was repeated 3 more times. 13-15 mg/mL ultra-low gelling temperature agarose (0.2-0.4 μL) was micropipetted once onto each network. If the gel drop did not wet the surface of the scaffold, then silver wire [ø0.1 mm, Sigma-Aldrich] was used to manipulate the droplet onto the scaffold, causing wetting. The coated scaffolds were then gelled (4° C., 20-25 min) and then either phase transferred straight away or stored in a hydration chamber.

Phase Transfer of Gel-Encapsulated Scaffolds:

The steps of the phase transfer of gel encapsulated scaffolds can be seen schematically in FIGS. 1A-1C. These steps were performed aseptically where possible, with scaffolds under oil treated as aseptic.

Phase Transfer of Coated Scaffolds

Two phase columns of a 3:1 v:v mix of hexadecane to mineral oil (~180 μL) above standard cell scaffold culture medium (~300 μL) were made in microscope chamber slides [154534K, Lab-Tek™] and then place in a cell incubator (15-60 min, 37° C., 5% $CO_{2(g)}$). The coated scaffolds were transferred by micropipette into the upper phase of the incubated column, typically one scaffold per column. If the coated scaffold did not spontaneously phase transfer, the chamber slide was mechanically perturbed by hand in a circular motion. With all scaffolds phase transferred, the upper oil phase was removed and additional standard cell scaffold culture medium (300 μL) was added. The chamber was then stored in the cell incubator (37° C., 5% $CO_{2(g)}$) until use.

Figure 2B:
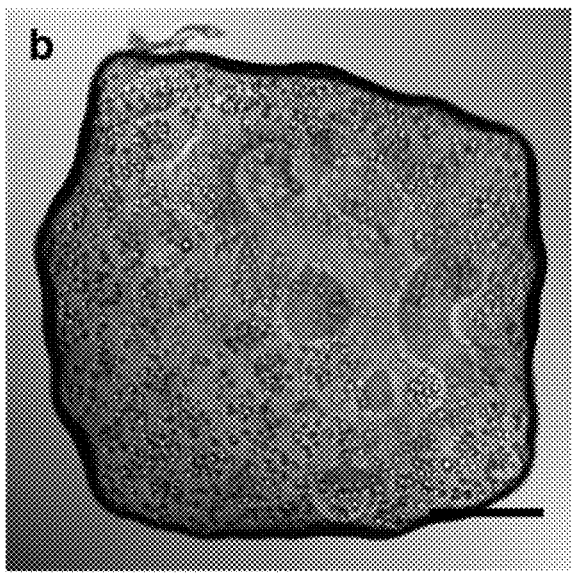
Figure 2C:
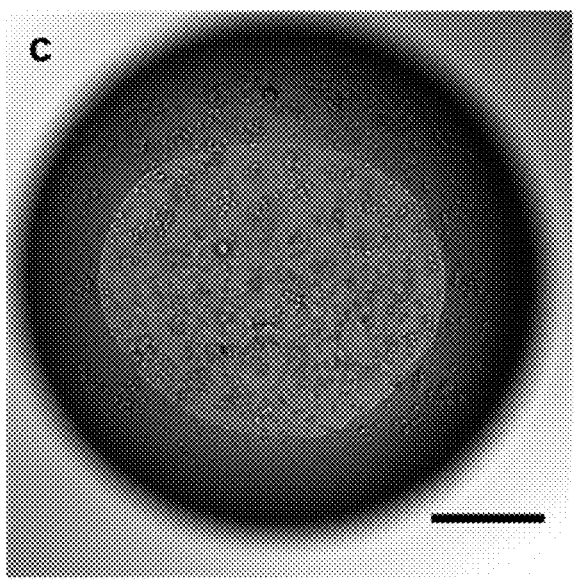
Figure 2D:
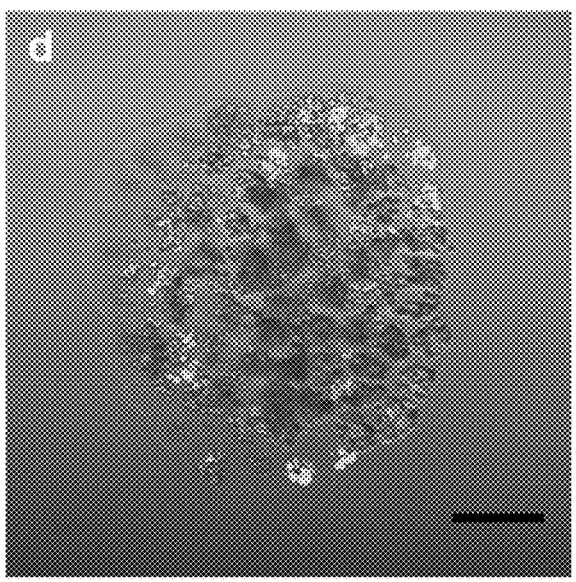

Micrographs of a first volume of hydrogel (i.e. a cell-laden scaffold) during coating with the second volume of hydrogel and subsequent phase transfer are shown in FIGS. 2A-2D. Bright-field confocal micrographs of independent printed oMSC networks at different points of the gelation and phase transfer process. These networks were printed with a bioink containing $5 \times 10^6$ cells mL$^{-1}$. FIG. 2A A gelled network under oil imaged immediately after gelation of the internal agarose. FIG. 2B The network of after dilution of the lipid and oil exchange. The droplet-droplet junctions are no longer visible. FIG. 2C A network coated in exterior ULGT agarose under oil, in this case more exterior gel than necessary had coated the network causing the structure to become spherical. FIG. 2D Gel-encapsulated printed network after transfer into culture medium, which contained live/dead cell dyes. No oil was transferred into the aqueous culture medium. Scale bars=250 μm.

Figure 3C:
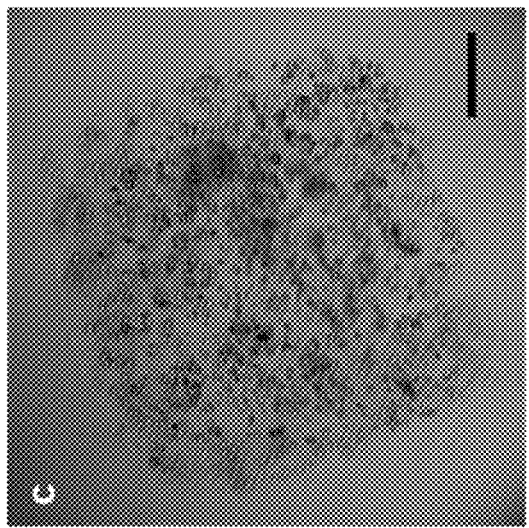
FIGS. 3A-3F show micrographs and fluorescence images of phase-transferred printed hydrogel scaffolds laden with biological cells.
Figure 3B:
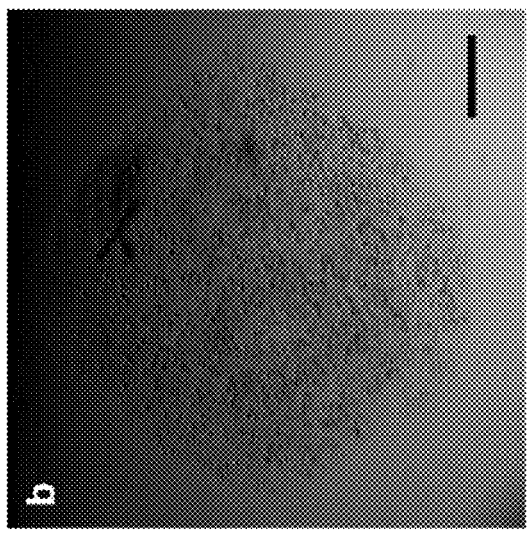
Figure 3A:
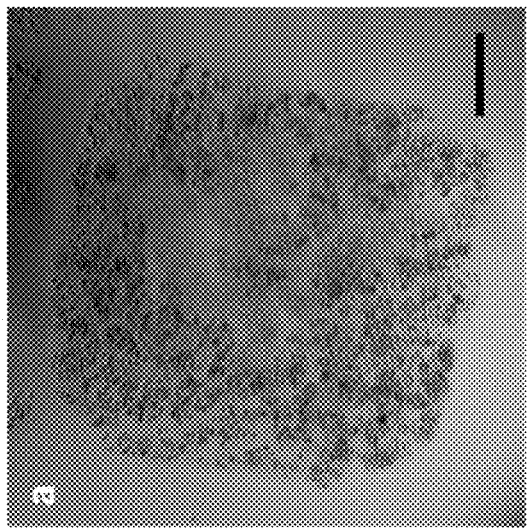
Figure 3F:
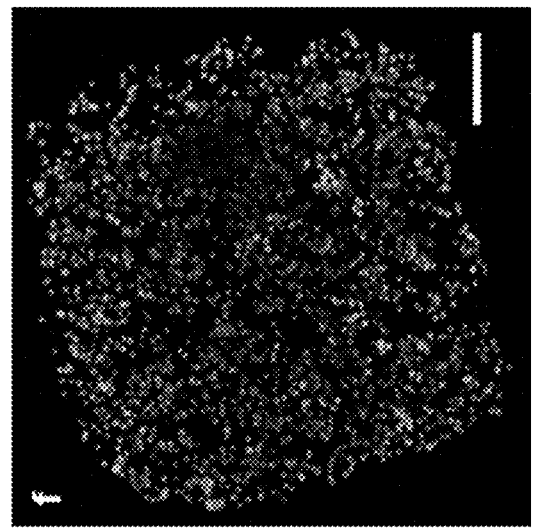
Figure 3E:
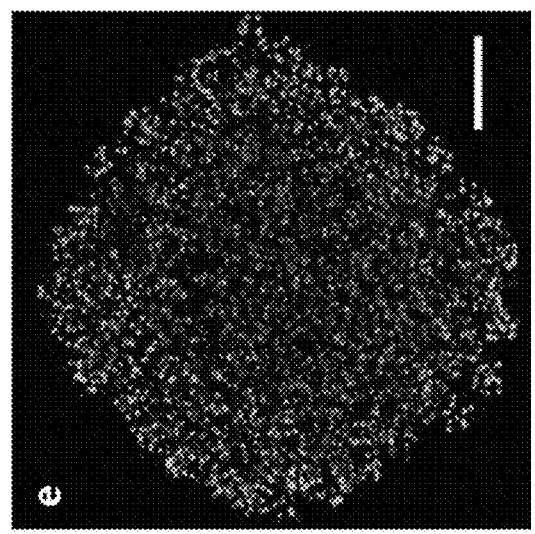
Figure 3D:
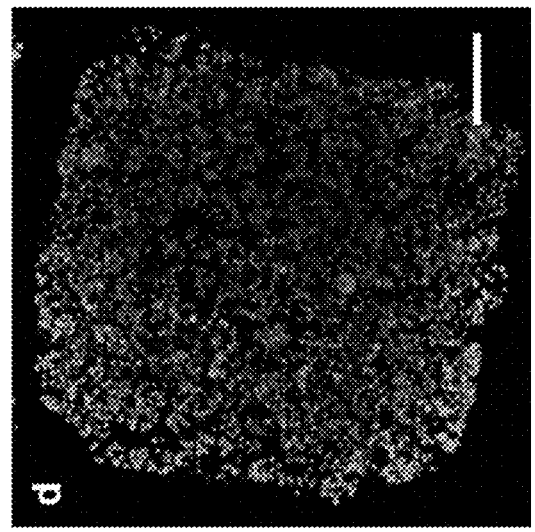
Figure 5A:
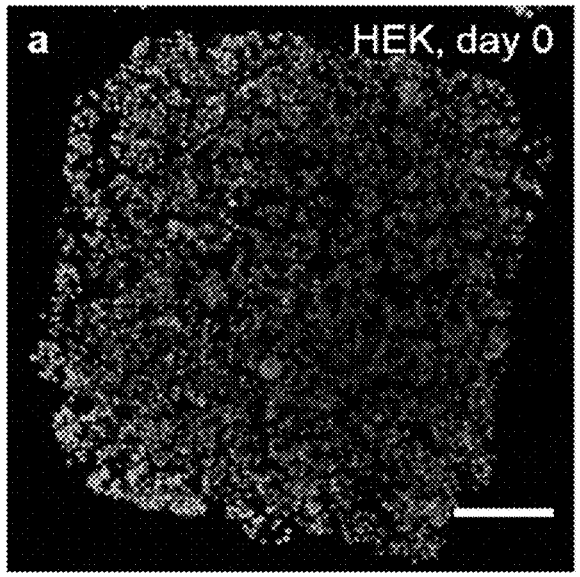
FIG. 5A-5D show micrographs and fluorescence images of biological cell development in phase-transferred printed hydrogel scaffolds over 7 days in culture.
Figure 5B:
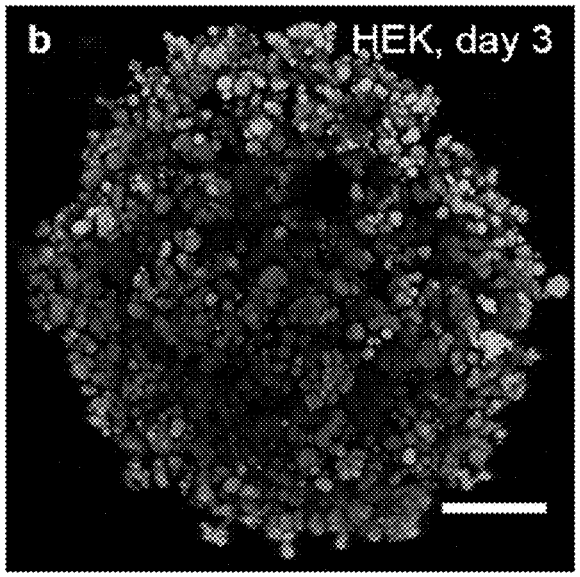
Figure 5C:
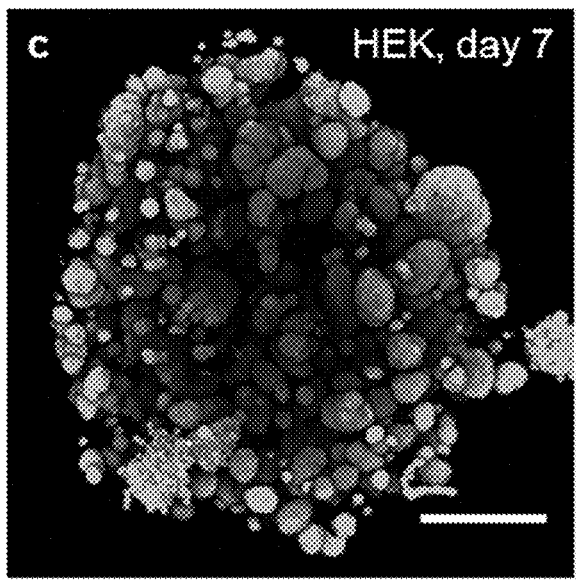
Figure 5D:
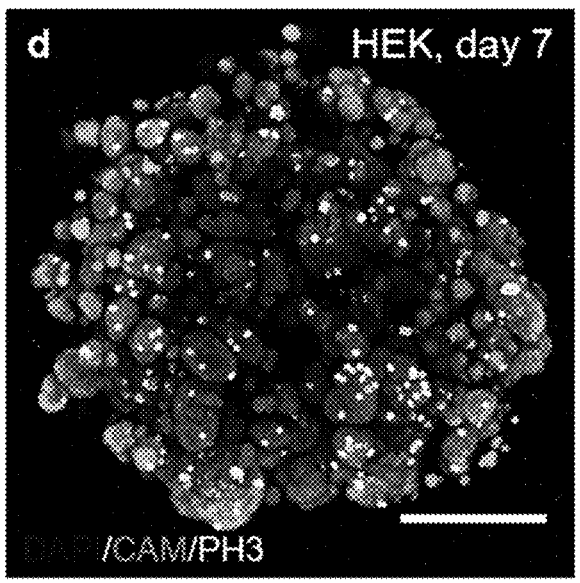

Volumes of hydrogel comprising scaffolds laden with either HEK-293T or oMSC cells were phase transferred by the process of the invention. The phase-transferred printed scaffolds containing homogeneous cells are shown in FIGS. 3A-3F. FIGS. 3A, 3B, 3C are bottom-up 3D projections of phase transferred homogenous cell scaffolds, stained by live-dead protocol with calcein-AM and propidium iodide leading to green staining for live cells and red staining for dead cells. FIGS. 3D, 3E, 3F are composite transmission and fluorescent images of scaffolds shown in FIGS. 3A, 3B, 3C respectively. Scaffolds FIGS. 3A/3D and FIGS. 3B/3E were printed HEK-293T at $15 \times 10^6$ cells/mL whilst scaffold FIGS. 3C/3F was printed oMSC at $15 \times 10^6$ cells/mL. All scaffolds contained 15 μg/mL collagen type I.

FIGS. 4A-4G show lamellar cell scaffolds after phase transfer to culture medium. Here lamellar cell scaffolds were patterned, by printing, as two adjoining layers of differing fluorescently tagged HEK cells. The results show that high resolution cell patterned features of scaffolds (such as these layers of ~200 μm thickness) were conserved during the phase transfer procedure. FIGS. 4A-4B show composite bright-field and fluorescence micrographs of a printed scaffold composed of two distinct cell layers imaged immediately after gelation (4° C., 20 min) at heights of (FIG. 4A) 45 μm and (FIG. 4B) 185 μm. HEK-293/YFP cells (yellow) were patterned below DR stained HEK-293/CFP cells (blue). (FIG. 4C) An illustration of a lamellar network, here, the lower droplets would contain HEK-293/YFP whilst the upper droplets would contain DR stained HEK-293/CFP. (FIGS. 4D-4E) Composite micrographs of the lamellar network in culture medium, imaged at heights of (FIG. 4D) 40 μm and (FIG. 4E) 180 μm, showing distinct cell layers. (FIGS. 4F-4G) Side-on image of a 3D reconstruction of the lamellar cell scaffold in: (FIG. 4F) oil immediately after printing and; (FIG. 4G) culture medium immediately after phase transfer, demonstrating that the lamellar cell pattern was conserved throughout.

FIGS. 5A-5D show the development of cells within phase-transferred scaffolds over 7 days in culture. The cells were stained using the live-dead staining protocol, revealing cells had high viability and had increased cellular mass over 7 days culture. Immunocytochemistry of cells on day 7, revealed healthy cell nuclei throughout the structure and a low proportion of mitotically active cells indicating the cells had proliferated. (FIGS. 5A-5C) Images of 3D reconstructions of printed HEK-293T cell scaffolds in culture on day: (FIG. 5A) 0; (FIG. 5B) 3 and (FIG. 5C) 7. Structures were stained for live cells (calcein-AM) and dead cells (propidium iodide). Printed cells in gel-encapsulated scaffolds were highly viable and showed an increased in cellular density over culture. (FIG. 5D) Image of a 3D reconstruction of the scaffold in (FIG. 5C) after staining for cell nuclei (DAPI) and the mitotic marker phosphohistone-H3 (PH3, immunocytochemistry, white). The scaffold displayed a low proportion of mitotically active cells, confirming the cellular proliferation within scaffolds.

Cell Scaffold Maintenance

The cells within phase-transferred scaffolds were grown in culture medium (~600 μL per well) for up to 14 days using a microscope chamber slides [154534K, Lab-Tek™] container. Scaffolds were stored between medium exchanges and experimentation in a Midi 40 cell incubator [Thermo Scientific] set at 37° C. with 5% $CO_{2(g)}$. Every 2-3 days the scaffolds medium was exchanged, for a single well this was as follows: ~200-300 μL container medium was carefully removed near the air-medium interface and then 300 μL fresh medium was added slowly at corner of the well, this container-medium removal, fresh-medium addition step was repeated 1-2 more time(s).

The majority of HEK-293T and fluorescent HEK-293 scaffolds were cultured in fully supplemented standard cell scaffold culture medium. However, initial HEK-293T scaffolds were cultured without antibiotics, HEPES and MEM non-essential amino acids (in earlier cell scaffold culture medium).

The oMSC scaffolds were cultured in MSC culture medium for standard viability assessment, and for differentiation experiments MSC differentiation medium or MSC control medium was used.

Live/Dead Assay

Live/dead staining of cell networks was performed by using a calcein-AM (CAM) dye (Cambridge Biosciences Ltd) in conjunction with propidium iodide (PI, Sigma Aldrich). A dye solution of 0.05 mM CAM and 0.05 mM PI was added to the cell-laden bioink prior to printing or to the culture medium of printed networks at a final concentration of ~5 μM for each component. Networks were imaged by fluorescence confocal microscopy (Leica SP5).

Networks Containing Two Cell Populations

CellTracker™ dyes (Life-Technologies), Red CMPTX (RC) and Deep Red (DR), were used to fluorescently stain cells. Prior to printing, the cells were suspended in serum-free culture medium containing either 5 μM RC or 1 μM DR. The cells stained were: HEK-293T, CFP expressing HEK-293, primary chondrocytes and oMSC-derived osteoblasts. Printed networks were imaged by fluorescence confocal microscopy (Leica SP5) and wide-field light microscopy (Leica DMI 8).

Immunocytochemistry of Printed Networks

Immunocytochemistry was performed on cell networks fixed in paraformaldehyde (Supplementary Methods). Primary antibodies were: 0.25% v/v rabbit anti-phosphohistone H3 (Merck Millipore) or 0.67% v/v rabbit anti-SOX-9 (Merck Millipore). Secondary donkey antibodies conjugated to Alexa Fluor 568 or 647 (Invitrogen) were used with the SOX-9 and phosphohistone H3 antibodies, respectively. The immunostained networks were imaged by fluorescence confocal microscopy (Zeiss LSM 710)

Formulation of Cell Culture Media:

Formulations of cell culture media used to grow 2D cell colonies or cells within phase-transferred scaffolds.

Cell-Culture Media Mixtures

Each cell type has its own specific cell culture medium composition. All culture media were composed of essential medium with or without the following supplements: 10% v/v FBS, 2 mM GlutaMAX™ (which is a source of glutamine), 0.1 mM MEM non-essential amino acids, 10-25 mM HEPES (buffering agent), 100 U/mL penicillin (an antibiotic) and 100 μg/mL streptomycin (an antibiotic). The ratio of these components can be seen in Table 4.

The base medium varied between the different cell lines and was either DMEM or MEM. Specifically three different DMEM culture media were used throughout the culture of most cell lines, these are now described along with their Sigma-Aldrich product codes: DMEM D6546 was, a high glucose medium, and used for all HEK-293 cell-line derivatives; DMEM D5564 was, a low glucose medium, and used in the culture of MSCs; whilst DMEM D5671 was, a high glucose medium with no sodium pyruvate, and used to make DMEM-ITS base medium for the differentiation experiments of the MSCs. Each DMEM contained either high (4500 mg/L) or low (1000 mg/mL) glucose with sodium bicarbonate, pyridoxine hydrochloride and 10 mg/L sodium pyruvate (unless stated). For osteogenic differentiation of MSCs and culture of osteoblasts, MEM M4526 was used, and contained sodium bicarbonate and increased amino acid concentrations compared to standard MEM. The base medium of each cell-line's culture medium is also described in Table 4.

Additional nutrients or special antibiotics were also used for all cell-lines but standard 2D culture of HEK-293T. These are described below for each cell type.

TABLE 4

Compositions for standard culture media used to grow the various cell-lines. The 100× concentrated stocks are 200 mM L-alanyl-L-glutamine (GlutaMAX ™), 10 mM MEM-NEAA, and 10,000 U/mL penicillin with 10,000 μg/mL streptomycin (PenStrep).

| | | Media Composition | | | | | |
| --- | --- | --- | --- | --- | --- | --- | --- |
| Medium Type | Base Medium | FBS (% v/v) | GlutaMAX ™ (100×) (% v/v) | 100× MEM-NEAA (% v/v) | 1M HEPES (% v/v) | 100× PenStrep (% v/v) | Additional Nutrients |
| HEK-293T Culture | DMEM D6546 | 10 | 1 | 0 | 0 | 0 | No |
| HEK-293/xFP Culture | DMEM D6546 | 10 | 1 | 1 | 0 | 0 | No |
| Original Cell Scaffold Culture | DMEM D6546 | 10 | 1 | 0 | 0 | 0 | No |

TABLE 4-continued

Compositions for standard culture media used to grow the various cell-lines. The 100× concentrated stocks are 200 mM L-alanyl-L-glutamine (GlutaMAX ™), 10 mM MEM-NEAA, and 10,000 U/mL penicillin with 10,000 μg/mL streptomycin (PenStrep).

| Medium Type | Base Medium | FBS (% v/v) | GlutaMAX ™ (100×) (% v/v) | 100× MEM-NEAA (% v/v) | 1M HEPES (% v/v) | 100× PenStrep (% v/v) | Additional Nutrients |
|---|---|---|---|---|---|---|---|
| Standard Cell Scaffold Culture | DMEM D6546 | 10 | 1 | 1 | 1 | 1 | No |
| MSC Culture | DMEM D5564 | 10 | 1 | 0 | 0 | 1 | Yes |
| MSC Differentiation | DMEM D5671 | 0 | 1 | 0 | 1-2 | 1 | Yes |
| MSC Control | DMEM D5671 | 0 | 1 | 0 | 1-2 | 1 | Yes |
| Chondrocyte Culture | DMEM D5564 | 10 | 1 | 0 | 0 | 1 | Yes |
| Osteoblast Culture | MEM M4526 | 10 | 1 | 0 | 0 | 1 | Yes |

Fluorescent HEK-293 Culture Medium

For the culture of fluorescent protein expressing HEK-293 cells 10 μg/mL blasticidin was also added. Stock blasticidin solution (10 mg/mL) was prepared by dissolving blasticidin powder (50 mg) in filter sterilised ultrapure water (5 mL) and stored as 10 μL aliquots at −20° C. The stock solution was added at 1 μL/mL per culture flask.

Ovine MSC and Chondrocyte Culture Medium

All oMSC media involved additional supplements; for the MSC culture, the medium also contained 5 ng/mL FGF, added just before time of use from a 10 μg/mL FGF stock. Chondrocyte culture medium was exactly the same as the MSC culture medium. Stock 10 μg/mL FGF solution was made by dissolving FGF (50 μg) in filter-sterilised 5 mM Tris HCl solution (5 mL, pH 7.6), with aliquots stored at −20° C.

Ovine MSC Differentiation Media

For MSCs differentiation experiments, the cells are cultured in MSC differentiation medium or MSC control medium, the base medium of which is called DMEM-ITS and comprised of DMEM D5671, un-supplemented with FBS, but containing ITS (at 10.0 μg/mL bovine insulin, 5.5 μg/mL human transferrin and 6.7 ng/mL sodium selenite), 1 mM sodium pyruvate, 2 mM GlutaMAX™, 100 U/mL penicillin and 100 μg/mL streptomycin. The MSC differentiation medium for day 0-7 also contained 100 nM dexamethasone, 80 μM ascorbic acid-2-phosphate and 10 ng/mL TGF-β3, all freshly supplemented. After day 7 the MSC differentiation medium additionally included 10 ng/mL insulin, also added fresh. Whereas the MSC control medium is the same as MSC differentiation media for day 0-7, but without the TGF-β3. A summary of additional nutrient supplements for MSC culture can be seen in Table 5.

The additional nutrients, dexamethasone, ascorbic acid, TGFβ3 and insulin, were all prepared from powdered reagents to give stock solutions which were vortexed mixed and then filter-sterilised and stored as aliquots at −20° C. The 100 μM dexamethasone stock was prepared by dissolving dexamethasone (3.925 mg) in ethanol (1 mL) and then further diluted to a 0.01% (v/v) solution in ITS-DMEM (1 mL). For ascorbate, the 80 mM stock was made by dissolving L-ascorbic acid 2-phosphate sesquimagnesium salt hydrate in ultrapure water (3 mL). The 10 μg/mL TGF-β3 stock was created by dissolving TGF-β3 in filter sterilised 4 mM hydrochloric acid containing 1 mg/mL BSA. Finally, the 10 mg/mL stock insulin was prepared by dissolving insulin (20 mg) in ultrapure water diluted acetic acid (2 mL, pH 2.0).

TABLE 5

Proportion of additional nutrient supplements added to the MSC media. The nutrients added are from stock solutions which are as follows, 100× concentrated ITS (at 1.00 mg/mL bovine insulin, 0.55 mg/mL human transferrin and 0.67 μg/mL sodium selenite), 100× concentrate sodium pyruvate (100 mM), 10 μg/mL FGF, 100 μM dexamethasone, 80 mM ascorbic acid-2-phosphate, 10 μg/mL TGF-β3 and 10 mg/mL insulin.

| Media Type | ITS (% v/v) | Sodium Pyruvate (% v/v) | FGF μL/mL | Ascorbic Acid μL/mL | Dexamethasone μL/mL | TGF-β3 μL/mL | Insulin μL/mL |
|---|---|---|---|---|---|---|---|
| Chondrocyte/MSC Culture | 0 | 1 | 0.5 | 0.0 | 0.0 | 0.0 | 0.0 |
| MSC Differentiation (day 0-7) | 1 | 1 | 0.0 | 1.0 | 1.0 | 1.0 | 0.0 |
| MSC Differentiation (day >7) | 1 | 1 | 0.0 | 1.0 | 1.0 | 1.0 | 1.0 |
| MSC Control | 1 | 1 | 0.0 | 1.0 | 1.0 | 0.0 | 0.0 |

Osteoblast Culture Medium

For MSC osteogenesis, the osteoblast culture medium also contained 50 μL/mL StemXVivo™ osteogenic supplement, which was added as supplied on the day of use. Osteogenic supplement was stored as aliquots at −20° C.

The invention claimed is:

1. A process for producing a composition comprising an aqueous medium and, disposed in the aqueous medium, a first volume of a first hydrogel, which process comprises:
  (i) providing a composition comprising a first hydrophobic medium and, disposed in the first hydrophobic medium, a first volume of a first hydrogel;
  (ii) disposing a volume of an aqueous composition comprising a hydrogel compound around the first volume of the first hydrogel by: generating a droplet of the aqueous composition in the first hydrophobic medium; and, while the droplet of the aqueous composition and the first volume of the first hydrogel are both within the first hydrophobic medium, contacting the droplet of the aqueous composition with the first volume of the first hydrogel, so that the aqueous composition wets and coats the first volume of the first hydrogel;
  (iii) allowing the aqueous composition which coats the first volume of the first hydrogel to form a gel around the first volume of the first hydrogel, wherein said gel around the first volume of the first hydrogel is a second volume of a second hydrogel, and thereby forming a hydrogel object, which hydrogel object comprises:
    the first volume of the first hydrogel and
    the second volume of the second hydrogel around the first volume of the first hydrogel; and
  (iv) transferring the hydrogel object from the first hydrophobic medium to an aqueous medium and thereby producing the composition comprising the aqueous medium and, disposed in the aqueous medium, the first volume of the first hydrogel.

2. The process according to claim 1, wherein the first volume of the first hydrogel comprises one or more cargo items disposed therein.

3. The process according to claim 2, wherein the one or more cargo items are one or more biological cells.

4. The process according to claim 1, wherein the first volume of the first hydrogel further comprises a culture medium.

5. The process according to claim 1, wherein the first volume of the first hydrogel comprises a droplet assembly comprising a plurality of droplets of the first hydrogel.

6. The process according to claim 5, wherein the droplet assembly comprises a plurality of droplets of the first hydrogel arranged in a three dimensional structure and wherein each droplet in the three dimensional structure contacts at least one other droplet in the three dimensional structure.

7. The process according to claim 5, wherein the droplet assembly comprises 50 or more droplets of the first hydrogel.

8. The process according to claim 5, wherein the droplet assembly comprises:
  a first plurality of droplets of the first hydrogel, each of which droplets comprises one or more of a first type of biological cells disposed in the first hydrogel; and
  a second plurality of droplets of the first hydrogel, each of which droplets comprises one or more of a second type of biological cells disposed in the first hydrogel.

9. The process according to claim 5, wherein the droplet assembly comprises one or more droplets having a volume of from 0.001 to 100 nL.

10. The process according to claim 1, wherein the first hydrogel comprises a polysaccharide.

11. The process according to claim 1, wherein the first hydrophobic medium comprises a hydrocarbon compound and/or a silicone oil.

12. The process according to claim 1, wherein the first hydrophobic medium comprises a hydrocarbon and a silicone oil in a ratio (hydrocarbon):(silicone oil) of from 50:50 to 80:20 by volume.

13. The process according to claim 1, wherein the first hydrophobic medium comprises one or more amphipathic compounds at a total concentration of greater than zero and less than or equal to 0.1 mM.

14. The process according to claim 1, wherein the hydrogel compound is a polysaccharide.

15. The process according to claim 1, wherein the aqueous composition comprises the hydrogel compound at a concentration of from 1.0 to 20 mg/mL.

16. The process according to claim 1, wherein the total volume of the aqueous composition and the volume of first hydrogel is greater than or equal to 100 nL.

17. The process according to claim 1, wherein allowing the aqueous composition which coats the first volume of the first hydrogel to form a gel comprises cooling the aqueous composition comprising the hydrogel compound to a temperature of less than or equal to 10.0° C.

18. The process according to claim 1 wherein transferring the hydrogel object from the first hydrophobic medium to an aqueous medium comprises allowing the hydrogel object to move from a second hydrophobic medium into an aqueous medium.

19. The process according to claim 1 wherein transferring the hydrogel object from the first hydrophobic medium to an aqueous medium comprises:
  passing the hydrogel object through a first phase, which is a second hydrophobic medium, and into a second phase, which is an aqueous medium, and which second phase is in contact with the first phase.

20. The process according to claim 19, wherein the first phase has a lower density than the second phase and is disposed on the second phase, and passing the hydrogel object through the first phase and into the second phase comprises allowing the hydrogel object to fall through the first phase and into the second phase under the influence of gravity.

21. The process according to claim 1, which process further comprises, prior to (i):
  (a) providing a composition comprising an amphipathic molecule-containing hydrophobic medium with the first volume of the first hydrogel disposed therein; and
  (b) adding the first hydrophobic medium to the amphipathic molecule-containing hydrophobic medium, and optionally replacing at least part of the amphipathic molecule-containing hydrophobic medium with the first hydrophobic medium.

22. The process according to claim 21, wherein the first volume of the first hydrogel disposed in the amphipathic molecule-containing hydrophobic medium comprises one or more droplets of the first hydrogel, each of which one or more droplets of the first hydrogel comprises an outer layer of amphipathic molecules.

23. The process according to claim 1, wherein the first volume of the first hydrogel further comprises one or more biological cells disposed therein and wherein the process further comprises culturing the one or more biological cells.

24. The process according to claim 1, wherein the process further comprises:

isolating the hydrogel object from the aqueous medium.

25. The process according to claim 1 wherein the first volume of the first hydrogel further comprises: one or more biological cells disposed therein, and a culture medium.

* * * * *